(12) United States Patent
Haymond et al.

(10) Patent No.: US 12,138,405 B2
(45) Date of Patent: Nov. 12, 2024

(54) RAPIDLY INSERTABLE CENTRAL CATHETERS, ASSEMBLIES, AND METHODS THEREOF

(71) Applicant: Bard Access Systems, Inc., Salt Lake City, UT (US)

(72) Inventors: Bryan Haymond, Emigration Canyon, UT (US); Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 336 days.

(21) Appl. No.: 17/554,978

(22) Filed: Dec. 17, 2021

(65) Prior Publication Data

US 2022/0193377 A1    Jun. 23, 2022

Related U.S. Application Data

(60) Provisional application No. 63/126,997, filed on Dec. 17, 2020.

(51) Int. Cl.
| | | |
|---|---|---|
| *A61M 25/06* | (2006.01) | |
| *A61M 25/00* | (2006.01) | |
| *A61M 25/09* | (2006.01) | |

(52) U.S. Cl.
CPC .... *A61M 25/0631* (2013.01); *A61M 25/0097* (2013.01); *A61M 25/0606* (2013.01); *A61M 25/0637* (2013.01); *A61M 25/09* (2013.01)

(58) Field of Classification Search
CPC .......... A61M 25/0631; A61M 25/0097; A61M 25/0606; A61M 25/0637; A61M 25/09
See application file for complete search history.

(56) References Cited

U.S. PATENT DOCUMENTS

| 1,013,691 A | 1/1912 | Shields |
|---|---|---|
| 3,225,762 A | 12/1965 | Guttman |

(Continued)

FOREIGN PATENT DOCUMENTS

| DE | 202012006191 U1 | 7/2012 |
|---|---|---|
| EP | 0653220 A1 | 5/1995 |

(Continued)

OTHER PUBLICATIONS

PCT/US2022/039614 filed Aug. 5, 2022 International Search Report and Written Opinion dated Dec. 22, 2022.

(Continued)

*Primary Examiner* — Manuel A Mendez
(74) *Attorney, Agent, or Firm* — Rutan & Tucker LLP

(57) ABSTRACT

Disclosed herein are rapidly insertable central catheters ("RICCs"), RICC assemblies, and methods thereof. For example, a RICC can include a catheter tube, a suture wing disposed over a medial portion of the catheter tube, a hub coupled to a proximal portion of the catheter tube, and a number of extension legs extending from the hub. The catheter tube can include a first section in a distal portion of the catheter tube and a second section proximal of the first section. The suture wing can include a projection opposite a patient-facing side of the suture wing and a needle through hole through the projection. The needle through hole can be configured to accept a needle therethrough for insertion of the needle into a primary lumen of the catheter tube, which passes through a catheter-tube through hole through the suture wing. A method of the RICC can include using the RICC.

24 Claims, 7 Drawing Sheets

(56) References Cited

U.S. PATENT DOCUMENTS

| | | | |
|---|---|---|---|
| 3,382,872 A | 5/1968 | Rubin | |
| 3,570,485 A | 3/1971 | Reilly | |
| 3,890,976 A | 6/1975 | Bazell et al. | |
| 4,205,675 A | 6/1980 | Vaillancourt | |
| 4,292,970 A | 10/1981 | Hession, Jr. | |
| 4,468,224 A | 8/1984 | Enzmann et al. | |
| 4,525,157 A | 6/1985 | Vaillancourt | |
| 4,581,019 A | 4/1986 | Curelaru et al. | |
| 4,594,073 A | 6/1986 | Stine | |
| 4,702,735 A | 10/1987 | Luther et al. | |
| 4,743,265 A | 5/1988 | Whitehouse et al. | |
| 4,766,908 A | 8/1988 | Clement | |
| 4,863,432 A | 9/1989 | Kvalo | |
| 4,950,252 A | 8/1990 | Luther et al. | |
| 4,994,040 A | 2/1991 | Cameron et al. | |
| 5,017,259 A | 5/1991 | Kohsai | |
| 5,040,548 A | 8/1991 | Yock | |
| 5,057,073 A | 10/1991 | Martin | |
| 5,112,312 A | 5/1992 | Luther | |
| 5,115,816 A | 5/1992 | Lee | |
| 5,120,317 A | 6/1992 | Luther | |
| 5,158,544 A | 10/1992 | Weinstein | |
| 5,188,593 A | 2/1993 | Martin | |
| 5,195,962 A | 3/1993 | Martin et al. | |
| 5,207,650 A * | 5/1993 | Martin | A61M 25/0026 604/173 |
| RE34,416 E | 10/1993 | Lemieux | |
| 5,267,958 A | 12/1993 | Buchbinder et al. | |
| 5,295,970 A | 3/1994 | Clinton et al. | |
| 5,306,247 A | 4/1994 | Pfenninger | |
| 5,312,361 A | 5/1994 | Zadini et al. | |
| 5,322,512 A | 6/1994 | Mohiuddin | |
| 5,328,472 A | 7/1994 | Steinke et al. | |
| 5,350,358 A | 9/1994 | Martin | |
| 5,358,495 A | 10/1994 | Lynn | |
| 5,368,567 A | 11/1994 | Lee | |
| 5,378,230 A | 1/1995 | Mahurkar | |
| 5,380,290 A | 1/1995 | Makower et al. | |
| 5,389,087 A | 2/1995 | Miraki | |
| 5,439,449 A | 8/1995 | Mapes et al. | |
| 5,443,457 A | 8/1995 | Ginn et al. | |
| 5,460,185 A | 10/1995 | Johnson et al. | |
| 5,489,271 A | 2/1996 | Andersen | |
| 5,573,520 A | 11/1996 | Schwartz et al. | |
| 5,683,370 A * | 11/1997 | Luther | A61M 25/001 604/528 |
| 5,713,876 A | 2/1998 | Bogert et al. | |
| 5,718,678 A | 2/1998 | Fleming, III | |
| 5,772,636 A | 6/1998 | Brimhall et al. | |
| 5,885,251 A | 3/1999 | Luther | |
| 5,919,164 A | 7/1999 | Andersen | |
| 5,921,971 A | 7/1999 | Agro et al. | |
| 5,947,940 A | 9/1999 | Beisel | |
| 5,957,893 A | 9/1999 | Luther et al. | |
| 5,971,957 A | 10/1999 | Luther et al. | |
| 6,159,198 A | 12/2000 | Gardeski et al. | |
| 6,206,849 B1 | 3/2001 | Martin et al. | |
| 6,228,062 B1 | 5/2001 | Howell et al. | |
| 6,475,187 B1 | 11/2002 | Gerberding | |
| 6,551,284 B1 | 4/2003 | Greenberg et al. | |
| 6,606,515 B1 | 8/2003 | Windheuser et al. | |
| 6,616,630 B1 | 9/2003 | Woehr et al. | |
| 6,626,869 B1 | 9/2003 | Bint | |
| 6,638,252 B2 | 10/2003 | Moulton et al. | |
| 6,716,228 B2 | 4/2004 | Tal | |
| 6,726,659 B1 | 4/2004 | Stocking et al. | |
| 6,819,951 B2 | 11/2004 | Patel et al. | |
| 6,821,287 B1 | 11/2004 | Jang | |
| 6,926,692 B2 | 8/2005 | Katoh et al. | |
| 6,962,575 B2 | 11/2005 | Tal | |
| 6,991,625 B1 | 1/2006 | Gately et al. | |
| 6,994,693 B2 | 2/2006 | Tal | |
| 6,999,809 B2 | 2/2006 | Currier et al. | |
| 7,025,746 B2 | 4/2006 | Tal | |
| 7,029,467 B2 | 4/2006 | Currier et al. | |
| 7,037,293 B2 | 5/2006 | Carrillo et al. | |
| 7,074,231 B2 | 7/2006 | Jang | |
| 7,094,222 B1 | 8/2006 | Siekas et al. | |
| 7,141,050 B2 | 11/2006 | Deal et al. | |
| 7,144,386 B2 | 12/2006 | Korkor et al. | |
| 7,311,697 B2 | 12/2007 | Osborne | |
| 7,364,566 B2 | 4/2008 | Elkins et al. | |
| 7,377,910 B2 | 5/2008 | Katoh et al. | |
| 7,390,323 B2 | 6/2008 | Jang | |
| D600,793 S | 9/2009 | Bierman et al. | |
| D601,242 S | 9/2009 | Bierman et al. | |
| D601,243 S | 9/2009 | Bierman et al. | |
| 7,594,911 B2 | 9/2009 | Powers et al. | |
| 7,691,093 B2 | 4/2010 | Brimhall | |
| 7,722,567 B2 | 5/2010 | Tal | |
| D617,893 S | 6/2010 | Bierman et al. | |
| D624,643 S | 9/2010 | Bierman et al. | |
| 7,819,889 B2 | 10/2010 | Healy et al. | |
| 7,857,788 B2 | 12/2010 | Racz | |
| D630,729 S | 1/2011 | Bierman et al. | |
| 7,909,797 B2 | 3/2011 | Kennedy, II et al. | |
| 7,909,811 B2 | 3/2011 | Agro et al. | |
| 7,922,696 B2 | 4/2011 | Tal et al. | |
| 7,938,820 B2 | 5/2011 | Webster et al. | |
| 7,967,834 B2 | 6/2011 | Tal et al. | |
| 7,976,511 B2 | 7/2011 | Fojtik | |
| 7,985,204 B2 | 7/2011 | Katoh et al. | |
| 8,073,517 B1 | 12/2011 | Burchman | |
| 8,105,286 B2 | 1/2012 | Anderson et al. | |
| 8,192,402 B2 | 6/2012 | Anderson et al. | |
| 8,202,251 B2 | 6/2012 | Bierman et al. | |
| 8,206,356 B2 | 6/2012 | Katoh et al. | |
| 8,361,011 B2 | 1/2013 | Mendels | |
| 8,372,107 B2 | 2/2013 | Tupper | |
| 8,377,006 B2 | 2/2013 | Tal et al. | |
| 8,454,577 B2 | 6/2013 | Joergensen et al. | |
| 8,585,858 B2 * | 11/2013 | Kronfeld | A61M 25/0054 156/203 |
| 8,657,790 B2 | 2/2014 | Tal et al. | |
| 8,672,888 B2 | 3/2014 | Tal | |
| 8,696,645 B2 | 4/2014 | Tal et al. | |
| 8,784,362 B2 | 7/2014 | Boutilette et al. | |
| 8,827,958 B2 | 9/2014 | Bierman et al. | |
| 8,876,704 B2 | 11/2014 | Golden et al. | |
| 8,882,713 B1 | 11/2014 | Call et al. | |
| 8,900,192 B2 | 12/2014 | Anderson et al. | |
| 8,900,207 B2 | 12/2014 | Uretsky | |
| 8,915,884 B2 | 12/2014 | Tal et al. | |
| 8,956,327 B2 | 2/2015 | Bierman et al. | |
| 9,023,093 B2 | 5/2015 | Pal | |
| 9,067,023 B2 | 6/2015 | Bertocci | |
| 9,126,012 B2 | 9/2015 | McKinnon et al. | |
| 9,138,252 B2 | 9/2015 | Bierman et al. | |
| 9,180,275 B2 | 11/2015 | Helm | |
| 9,265,920 B2 | 2/2016 | Rundquist et al. | |
| 9,272,121 B2 | 3/2016 | Piccagli | |
| 9,445,734 B2 | 9/2016 | Grunwald | |
| 9,522,254 B2 | 12/2016 | Belson | |
| 9,554,785 B2 | 1/2017 | Walters et al. | |
| 9,566,087 B2 | 2/2017 | Bierman et al. | |
| 9,675,784 B2 | 6/2017 | Belson | |
| 9,713,695 B2 | 7/2017 | Bunch et al. | |
| 9,764,117 B2 | 9/2017 | Bierman et al. | |
| 9,770,573 B2 | 9/2017 | Golden et al. | |
| 9,814,861 B2 | 11/2017 | Boutilette et al. | |
| 9,820,845 B2 | 11/2017 | von Lehe et al. | |
| 9,861,383 B2 | 1/2018 | Clark | |
| 9,872,971 B2 | 1/2018 | Blanchard | |
| 9,884,169 B2 | 2/2018 | Bierman et al. | |
| 9,889,275 B2 | 2/2018 | Voss et al. | |
| 9,913,585 B2 | 3/2018 | McCaffrey et al. | |
| 9,913,962 B2 | 3/2018 | Tal et al. | |
| 9,981,113 B2 | 5/2018 | Bierman | |
| 10,010,312 B2 | 7/2018 | Tegels | |
| 10,065,020 B2 | 9/2018 | Gaur | |
| 10,086,170 B2 | 10/2018 | Chhikara et al. | |
| 10,098,724 B2 | 10/2018 | Adams et al. | |
| 10,111,683 B2 | 10/2018 | Tsamir et al. | |
| 10,118,020 B2 | 11/2018 | Avneri et al. | |

(56) References Cited

U.S. PATENT DOCUMENTS

| | | |
|---|---|---|
| 10,130,269 B2 | 11/2018 | McCaffrey et al. |
| 10,220,184 B2 | 3/2019 | Clark |
| 10,220,191 B2 | 3/2019 | Belson et al. |
| 10,265,508 B2 | 4/2019 | Baid |
| 10,271,873 B2 | 4/2019 | Steingisser et al. |
| 10,376,675 B2 * | 8/2019 | Mitchell ............ A61M 25/0606 |
| 10,675,440 B2 | 6/2020 | Abitabilo et al. |
| 10,806,901 B2 | 10/2020 | Burkholz et al. |
| 10,926,060 B2 | 2/2021 | Stern et al. |
| 11,260,206 B2 | 3/2022 | Stone et al. |
| 11,759,607 B1 | 9/2023 | Biancarelli |
| 2002/0040231 A1 | 4/2002 | Wysoki |
| 2002/0198492 A1 | 12/2002 | Miller et al. |
| 2003/0036712 A1 | 2/2003 | Heh et al. |
| 2003/0060863 A1 | 3/2003 | Dobak |
| 2003/0088212 A1 | 5/2003 | Tal |
| 2003/0100849 A1 | 5/2003 | Jang |
| 2003/0153874 A1 | 8/2003 | Tal |
| 2003/0158514 A1 | 8/2003 | Tal |
| 2004/0015138 A1 | 1/2004 | Currier et al. |
| 2004/0064086 A1 | 4/2004 | Gottlieb et al. |
| 2004/0116864 A1 | 6/2004 | Boudreaux |
| 2004/0116901 A1 | 6/2004 | Appling |
| 2004/0167478 A1 | 8/2004 | Mooney et al. |
| 2004/0193093 A1 | 9/2004 | Desmond |
| 2004/0230178 A1 | 11/2004 | Wu |
| 2005/0004554 A1 | 1/2005 | Osborne |
| 2005/0120523 A1 | 6/2005 | Schweikert |
| 2005/0131343 A1 | 6/2005 | Abrams et al. |
| 2005/0215956 A1 | 9/2005 | Nerney |
| 2005/0245882 A1 | 11/2005 | Elkins et al. |
| 2005/0283221 A1 | 12/2005 | Mann et al. |
| 2006/0009740 A1 | 1/2006 | Higgins et al. |
| 2006/0116629 A1 | 6/2006 | Tal et al. |
| 2006/0129100 A1 | 6/2006 | Tal |
| 2006/0129130 A1 | 6/2006 | Tal et al. |
| 2007/0276288 A1 | 11/2007 | Khaw |
| 2008/0045894 A1 | 2/2008 | Perchik et al. |
| 2008/0125744 A1 | 5/2008 | Treacy |
| 2008/0125748 A1 | 5/2008 | Patel |
| 2008/0132850 A1 | 6/2008 | Fumiyama et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0312578 A1 | 12/2008 | DeFonzo et al. |
| 2008/0319387 A1 | 12/2008 | Amisar et al. |
| 2009/0187147 A1 | 7/2009 | Kurth et al. |
| 2009/0221961 A1 | 9/2009 | Tal et al. |
| 2009/0270889 A1 | 10/2009 | Tal et al. |
| 2009/0292272 A1 | 11/2009 | McKinnon |
| 2010/0030154 A1 | 2/2010 | Duffy |
| 2010/0256487 A1 | 10/2010 | Hawkins et al. |
| 2010/0298839 A1 | 11/2010 | Castro |
| 2010/0305474 A1 | 12/2010 | DeMars et al. |
| 2011/0004162 A1 | 1/2011 | Tal |
| 2011/0009827 A1 | 1/2011 | Bierman et al. |
| 2011/0021994 A1 | 1/2011 | Anderson et al. |
| 2011/0066142 A1 | 3/2011 | Tal et al. |
| 2011/0071502 A1 | 3/2011 | Asai |
| 2011/0144620 A1 | 6/2011 | Tal |
| 2011/0152836 A1 | 6/2011 | Riopelle et al. |
| 2011/0202006 A1 | 8/2011 | Bierman et al. |
| 2011/0251559 A1 | 10/2011 | Tal et al. |
| 2011/0270192 A1 | 11/2011 | Anderson et al. |
| 2012/0041371 A1 | 2/2012 | Tal et al. |
| 2012/0065590 A1 | 3/2012 | Bierman et al. |
| 2012/0078231 A1 | 3/2012 | Hoshinouchi |
| 2012/0130411 A1 | 5/2012 | Tal et al. |
| 2012/0130415 A1 | 5/2012 | Tal et al. |
| 2012/0157854 A1 | 6/2012 | Kurrus et al. |
| 2012/0215171 A1 | 8/2012 | Christiansen |
| 2012/0220942 A1 | 8/2012 | Hall et al. |
| 2012/0226239 A1 | 9/2012 | Green |
| 2012/0283640 A1 | 11/2012 | Anderson et al. |
| 2012/0316500 A1 | 12/2012 | Bierman et al. |
| 2013/0053763 A1 | 2/2013 | Makino et al. |
| 2013/0053826 A1 | 2/2013 | Shevgoor |
| 2013/0123704 A1 | 5/2013 | Bierman et al. |
| 2013/0158338 A1 | 6/2013 | Kelly et al. |
| 2013/0188291 A1 | 7/2013 | Vardiman |
| 2013/0237931 A1 | 9/2013 | Tal et al. |
| 2013/0306079 A1 | 11/2013 | Tracy |
| 2014/0025036 A1 | 1/2014 | Bierman et al. |
| 2014/0081210 A1 | 3/2014 | Bierman et al. |
| 2014/0094774 A1 | 4/2014 | Blanchard |
| 2014/0100552 A1 | 4/2014 | Gallacher et al. |
| 2014/0207052 A1 | 7/2014 | Tal et al. |
| 2014/0207069 A1 | 7/2014 | Bierman et al. |
| 2014/0214005 A1 | 7/2014 | Belson |
| 2014/0257111 A1 | 9/2014 | Yamashita et al. |
| 2014/0276432 A1 | 9/2014 | Bierman et al. |
| 2014/0276599 A1 | 9/2014 | Cully et al. |
| 2015/0011834 A1 | 1/2015 | Ayala et al. |
| 2015/0080939 A1 | 3/2015 | Adams et al. |
| 2015/0094653 A1 | 4/2015 | Pacheco et al. |
| 2015/0112307 A1 | 4/2015 | Margolis |
| 2015/0112310 A1 | 4/2015 | Call et al. |
| 2015/0126930 A1 | 5/2015 | Bierman et al. |
| 2015/0148595 A1 | 5/2015 | Bagwell et al. |
| 2015/0190168 A1 | 7/2015 | Bierman et al. |
| 2015/0196210 A1 | 7/2015 | McCaffrey et al. |
| 2015/0224287 A1 | 8/2015 | Bian et al. |
| 2015/0231364 A1 | 8/2015 | Blanchard et al. |
| 2015/0283357 A1 | 10/2015 | Lampropoulos et al. |
| 2015/0297868 A1 | 10/2015 | Tal et al. |
| 2015/0320969 A1 | 11/2015 | Haslinger et al. |
| 2015/0320977 A1 | 11/2015 | Vitullo et al. |
| 2015/0351793 A1 | 12/2015 | Bierman et al. |
| 2015/0359549 A1 | 12/2015 | Lenker et al. |
| 2015/0359998 A1 | 12/2015 | Carmel et al. |
| 2016/0082223 A1 | 3/2016 | Barnell |
| 2016/0114124 A1 | 4/2016 | Tal |
| 2016/0158523 A1 | 6/2016 | Helm |
| 2016/0220786 A1 | 8/2016 | Mitchell et al. |
| 2016/0242661 A1 | 8/2016 | Fischell et al. |
| 2016/0256101 A1 | 9/2016 | Aharoni et al. |
| 2016/0325073 A1 | 11/2016 | Davies et al. |
| 2016/0338728 A1 | 11/2016 | Tal |
| 2016/0346503 A1 | 12/2016 | Jackson et al. |
| 2017/0035990 A1 | 2/2017 | Swift |
| 2017/0072165 A1 | 3/2017 | Lim et al. |
| 2017/0120000 A1 | 5/2017 | Osypka et al. |
| 2017/0120014 A1 | 5/2017 | Harding et al. |
| 2017/0120034 A1 | 5/2017 | Kaczorowski |
| 2017/0128700 A1 | 5/2017 | Roche Rebollo |
| 2017/0156987 A1 | 6/2017 | Babbs et al. |
| 2017/0172653 A1 | 6/2017 | Urbanski et al. |
| 2017/0182293 A1 | 6/2017 | Chhikara et al. |
| 2017/0239443 A1 | 8/2017 | Abitabilo et al. |
| 2017/0259043 A1 | 9/2017 | Chan et al. |
| 2017/0273713 A1 | 9/2017 | Shah et al. |
| 2017/0296792 A1 | 10/2017 | Ornelas Vargas et al. |
| 2017/0326339 A1 | 11/2017 | Bailey et al. |
| 2017/0361070 A1 | 12/2017 | Hivert |
| 2017/0368255 A1 | 12/2017 | Provost et al. |
| 2018/0001062 A1 | 1/2018 | O'Carrol et al. |
| 2018/0021545 A1 | 1/2018 | Mitchell et al. |
| 2018/0116690 A1 | 5/2018 | Sarabia et al. |
| 2018/0117284 A1 | 5/2018 | Appling et al. |
| 2018/0133438 A1 | 5/2018 | Hulvershorn et al. |
| 2018/0154062 A1 | 6/2018 | DeFonzo et al. |
| 2018/0154112 A1 | 6/2018 | Chan et al. |
| 2018/0214674 A1 | 8/2018 | Ebnet et al. |
| 2018/0296799 A1 | 10/2018 | Horst et al. |
| 2018/0296804 A1 | 10/2018 | Bierman |
| 2018/0310955 A1 | 11/2018 | Lindekugel et al. |
| 2019/0015646 A1 | 1/2019 | Matlock et al. |
| 2019/0021640 A1 * | 1/2019 | Burkholz ............... A61B 5/153 |
| 2019/0060616 A1 | 2/2019 | Solomon |
| 2019/0076167 A1 | 3/2019 | Fantuzzi et al. |
| 2019/0134349 A1 | 5/2019 | Cohn et al. |
| 2019/0192824 A1 | 6/2019 | Cordeiro et al. |
| 2019/0201665 A1 | 7/2019 | Turpin |
| 2019/0209812 A1 | 7/2019 | Burkholz et al. |

(56) References Cited

U.S. PATENT DOCUMENTS

| | | |
|---|---|---|
| 2019/0255294 A1 | 8/2019 | Mitchell et al. |
| 2019/0255298 A1 | 8/2019 | Mitchell et al. |
| 2019/0275303 A1 | 9/2019 | Tran et al. |
| 2019/0276268 A1 | 9/2019 | Akingba |
| 2019/0321590 A1 | 10/2019 | Burkholz et al. |
| 2020/0001051 A1 | 1/2020 | Huang et al. |
| 2020/0016374 A1 | 1/2020 | Burkholz et al. |
| 2020/0046948 A1 | 2/2020 | Burkholz et al. |
| 2020/0100716 A1 | 4/2020 | Devgon et al. |
| 2020/0129732 A1 | 4/2020 | Vogt et al. |
| 2020/0147349 A1 | 5/2020 | Holt |
| 2020/0197682 A1 | 6/2020 | Franklin et al. |
| 2020/0197684 A1 | 6/2020 | Wax |
| 2020/0237278 A1 | 7/2020 | Asbaghi |
| 2020/0359995 A1 | 11/2020 | Walsh et al. |
| 2021/0030944 A1 | 2/2021 | Cushen et al. |
| 2021/0060306 A1 | 3/2021 | Kumar |
| 2021/0069471 A1 | 3/2021 | Howell |
| 2021/0085927 A1 | 3/2021 | Howell |
| 2021/0100985 A1 | 4/2021 | Akcay et al. |
| 2021/0113809 A1 | 4/2021 | Howell |
| 2021/0113810 A1 | 4/2021 | Howell |
| 2021/0113816 A1 | 4/2021 | DiCianni |
| 2021/0121661 A1 | 4/2021 | Howell |
| 2021/0121667 A1 | 4/2021 | Howell |
| 2021/0228842 A1 | 7/2021 | Scherich et al. |
| 2021/0228843 A1 | 7/2021 | Howell et al. |
| 2021/0244920 A1 | 8/2021 | Kujawa et al. |
| 2021/0290898 A1 | 9/2021 | Burkholz |
| 2021/0290901 A1 | 9/2021 | Burkholz et al. |
| 2021/0290913 A1 | 9/2021 | Horst et al. |
| 2021/0322729 A1 | 10/2021 | Howell |
| 2021/0330941 A1 | 10/2021 | Howell et al. |
| 2021/0330942 A1 | 10/2021 | Howell |
| 2021/0361915 A1 | 11/2021 | Howell et al. |
| 2021/0402149 A1 | 12/2021 | Howell |
| 2021/0402153 A1 | 12/2021 | Howell et al. |
| 2022/0001138 A1 | 1/2022 | Howell |
| 2022/0032013 A1 | 2/2022 | Howell et al. |
| 2022/0032014 A1 | 2/2022 | Howell et al. |
| 2022/0062528 A1 | 3/2022 | Thornley et al. |
| 2022/0126064 A1 | 4/2022 | Tobin et al. |
| 2022/0193376 A1 | 6/2022 | Spataro et al. |
| 2022/0193378 A1 | 6/2022 | Spataro et al. |
| 2022/0323723 A1 | 10/2022 | Spataro et al. |
| 2022/0331563 A1 | 10/2022 | Papadia |
| 2023/0042898 A1 | 2/2023 | Howell et al. |
| 2023/0096377 A1 | 3/2023 | West et al. |
| 2023/0096740 A1 | 3/2023 | Bechstein et al. |
| 2023/0099654 A1 | 3/2023 | Blanchard et al. |
| 2023/0100482 A1 | 3/2023 | Howell |
| 2023/0101455 A1 | 3/2023 | Howell et al. |
| 2023/0102231 A1 | 3/2023 | Bechstein et al. |
| 2023/0233814 A1 | 7/2023 | Howell et al. |
| 2024/0009427 A1 | 1/2024 | Howell et al. |
| 2024/0050706 A1 | 2/2024 | Howell et al. |
| 2024/0198058 A1 | 6/2024 | Howell et al. |

FOREIGN PATENT DOCUMENTS

| | | |
|---|---|---|
| EP | 0730880 A1 | 9/1996 |
| EP | 2061385 A1 | 5/2009 |
| EP | 1458437 B1 | 3/2010 |
| EP | 2248549 A2 | 11/2010 |
| EP | 2319576 A1 | 5/2011 |
| EP | 2366422 A1 | 9/2011 |
| EP | 2486880 A2 | 8/2012 |
| EP | 2486881 A2 | 8/2012 |
| EP | 2486951 A2 | 8/2012 |
| EP | 2512576 A2 | 10/2012 |
| EP | 2152348 B1 | 2/2015 |
| EP | 3473291 A1 | 4/2019 |
| EP | 3093038 B1 | 5/2019 |
| EP | 2260897 B1 | 9/2019 |
| EP | 3693051 A1 | 8/2020 |
| GB | 1273547 A | 5/1972 |
| JP | 2004248987 A | 9/2004 |
| JP | 2008054859 A | 3/2008 |
| WO | 94/21315 A1 | 9/1994 |
| WO | 95/32009 A2 | 11/1995 |
| WO | 98/44979 A1 | 10/1998 |
| WO | 98/53871 A1 | 12/1998 |
| WO | 99/12600 A1 | 3/1999 |
| WO | 99/26681 A1 | 6/1999 |
| WO | 00/06221 A1 | 2/2000 |
| WO | 0054830 A1 | 9/2000 |
| WO | 2003008020 A1 | 1/2003 |
| WO | 2003057272 A2 | 7/2003 |
| WO | 03/068073 A1 | 8/2003 |
| WO | 2003066125 A2 | 8/2003 |
| WO | 2005096778 A2 | 10/2005 |
| WO | 2006055288 A2 | 5/2006 |
| WO | 2006055780 A2 | 5/2006 |
| WO | 2007046850 A2 | 4/2007 |
| WO | 2008033983 A1 | 3/2008 |
| WO | 2008092029 A2 | 7/2008 |
| WO | 2008/131300 A2 | 10/2008 |
| WO | 2008131289 A2 | 10/2008 |
| WO | 2009114833 A1 | 9/2009 |
| WO | 2009114837 A2 | 9/2009 |
| WO | 2010/048449 A2 | 4/2010 |
| WO | 2010056906 A2 | 5/2010 |
| WO | 2010083467 A2 | 7/2010 |
| WO | 2010/132608 A2 | 11/2010 |
| WO | 2011081859 A2 | 7/2011 |
| WO | 2011097639 A2 | 8/2011 |
| WO | 2011109792 A1 | 9/2011 |
| WO | 2011146764 A1 | 11/2011 |
| WO | 2012068162 A2 | 5/2012 |
| WO | 2012068166 A2 | 5/2012 |
| WO | 2012135761 A1 | 10/2012 |
| WO | 2012/154277 A1 | 11/2012 |
| WO | 2012162677 A1 | 11/2012 |
| WO | 2013026045 A1 | 2/2013 |
| WO | 2013138519 A1 | 9/2013 |
| WO | 2014006403 A1 | 1/2014 |
| WO | 2014/100392 A1 | 6/2014 |
| WO | 2014113257 A2 | 7/2014 |
| WO | 2014152005 A2 | 9/2014 |
| WO | 2014197614 A2 | 12/2014 |
| WO | 2015057766 A1 | 4/2015 |
| WO | 2015077560 A1 | 5/2015 |
| WO | 2015/168655 A2 | 11/2015 |
| WO | 2016110824 A1 | 7/2016 |
| WO | 2016123278 A1 | 8/2016 |
| WO | 2016139590 A1 | 9/2016 |
| WO | 2016139597 A2 | 9/2016 |
| WO | 2016/178974 A1 | 11/2016 |
| WO | 2016/187063 A1 | 11/2016 |
| WO | 2016176065 A1 | 11/2016 |
| WO | 2018089275 A1 | 5/2018 |
| WO | 2018089285 A1 | 5/2018 |
| WO | 2018089385 A1 | 5/2018 |
| WO | 2018191547 A1 | 10/2018 |
| WO | 2018213148 A1 | 11/2018 |
| WO | 2018218236 A1 | 11/2018 |
| WO | 2019/050576 A1 | 3/2019 |
| WO | 2019/146026 A1 | 8/2019 |
| WO | 2019199734 A1 | 10/2019 |
| WO | 2020014149 A1 | 1/2020 |
| WO | 2020069395 A1 | 4/2020 |
| WO | 2020/109448 A1 | 6/2020 |
| WO | 2020/113123 A1 | 6/2020 |
| WO | 2021050302 A1 | 3/2021 |
| WO | 2021/077103 A1 | 4/2021 |
| WO | 2021062023 A1 | 4/2021 |
| WO | 2021081205 A1 | 4/2021 |
| WO | 2021086793 A1 | 5/2021 |
| WO | 2021/236950 A1 | 11/2021 |
| WO | 2022/031618 A1 | 2/2022 |
| WO | 2022/094141 A1 | 5/2022 |
| WO | 2022/133297 A1 | 6/2022 |
| WO | 2022-140406 A1 | 6/2022 |
| WO | 2022/140429 A1 | 6/2022 |

(56) References Cited

FOREIGN PATENT DOCUMENTS

| | | | |
|---|---|---|---|
| WO | 2022/217098 A1 | 10/2022 | |
| WO | 2023014994 A1 | 2/2023 | |
| WO | 2023049498 A1 | 3/2023 | |
| WO | 2023049505 A1 | 3/2023 | |
| WO | 2023049511 A1 | 3/2023 | |
| WO | 2023049519 A1 | 3/2023 | |
| WO | 2023049522 A1 | 3/2023 | |
| WO | 2023146792 A1 | 8/2023 | |

OTHER PUBLICATIONS

PCT/US2022/044848 filed Sep. 27, 2022 International Search Report and Written Opinion dated Feb. 3, 2023.
PCT/US2022/044879 filed Sep. 27, 2022 International Search Report and Written Opinion dated Mar. 3, 2023.
PCT/US2022/044901 filed Sep. 27, 2022 International Search Report and Written Opinion dated Mar. 3, 2023.
PCT/US2022/044918 filed Sep. 27, 2022 International Search Report and Written Opinion dated Feb. 21, 2023.
PCT/US2022/044923 filed Sep. 27, 2022 International Search Report and Written Opinion dated Feb. 15, 2023.
U.S. Appl. No. 17/156,252, filed Jan. 22, 2021 Notice of Allowance dated Apr. 24, 2023.
U.S. Appl. No. 17/237,909, filed Apr. 22, 2021 Restriction Requirement dated Feb. 1, 2023.
U.S. Appl. No. 17/326,017, filed May 20, 2021 Non-Final Office Action dated Jan. 26, 2023.
U.S. Appl. No. 17/390,682, filed Jul. 30, 2021 Non-Final Office Action dated Mar. 2, 2023.
U.S. Appl. No. 17/392,061, filed Aug. 2, 2021 Restriction Requirement dated Mar. 30, 2023.
U.S. Appl. No. 16/398,020, filed Apr. 29, 2019 Board Decision dated Oct. 30, 2023.
U.S. Appl. No. 16/398,020, filed Apr. 29, 2019 Non-Final Office Action dated Jan. 18, 2024.
U.S. Appl. No. 17/234,611, filed Apr. 19, 2021 Restriction Requirement dated Jan. 18, 2024.
U.S. Appl. No. 17/237,909, filed Apr. 22, 2021 Notice of Allowance dated Oct. 27, 2023.
U.S. Appl. No. 17/240,591, filed Apr. 26, 2021 Final Office Action dated Dec. 6, 2023.
U.S. Appl. No. 17/390,682, filed Jul. 30, 2021 Non-Final Office Action dated Dec. 1, 2023.
U.S. Appl. No. 17/392,061, filed Aug. 2, 2021 Final Office Action dated Nov. 21, 2023.
U.S. Appl. No. 17/513,789, filed Oct. 28, 2021 Non-Final Office Action dated Jan. 9, 2024.
U.S. Appl. No. 17/557,924, filed Dec. 21, 2021 Non-Final Office Action dated Nov. 3, 2023.
U.S. Appl. No. 17/156,252, filed Jan. 22, 2021 Notice of Allowance dated Aug. 9, 2023.
U.S. Appl. No. 17/237,909, filed Apr. 22, 2021 Non-Final Office Action dated Jul. 27, 2023.
U.S. Appl. No. 17/358,504, filed Jun. 25, 2021 Non-Final Office Action dated Oct. 4, 2023.
U.S. Appl. No. 17/360,694, filed Jun. 28, 2021 Non-Final Office Action dated Oct. 13, 2023.
U.S. Appl. No. 17/390,682, filed Jul. 30, 2021 Final Office Action dated Jul. 27, 2023.
U.S. Appl. No. 17/513,789, filed Oct. 28, 2021 Restriction Requirement dated Oct. 3, 2023.
PCT/US2021/028018 filed Apr. 19, 2021 International Preliminary Report on Patentability dated Jun. 3, 2022.
PCT/US2021/064174 filed Dec. 17, 2021 International Search Report and Written Opinion dated May 18, 2022.
PCT/US2021/064642 filed Dec. 21, 2021 International Search Report and Written Opinion dated May 11, 2022.
PCT/US2021/064671 filed Dec. 21, 2021 International Search Report and Written Opinion dated May 27, 2022.
PCT/US2022/024085 filed Apr. 8, 2022 International Search Report and Wirtten Opinion dated Sep. 12, 2022.
U.S. Appl. No. 16/398,020, filed Apr. 29, 2019 Examiner's Answer dated Oct. 31, 2022.
U.S. Appl. No. 17/031,478, filed Sep. 24, 2020 Notice of Allowance dated Sep. 16, 2022.
U.S. Appl. No. 17/156,252, filed Jan. 22, 2021 Non-Final Office Action dated Oct. 25, 2022.
PCT/US2021/044223 filed Aug. 2, 2021 International Search Report and Written Opinion dated Dec. 21, 2021.
PCT/US2021/048275 filed Aug. 30, 2021 International Search Report and Written Opinion dated Jan. 4, 2022.
U.S. Appl. No. 17/031,478, filed Sep. 24, 2020 Non-Final Office Action dated May 11, 2022.
PCT/US2021/057135 filed Oct. 28, 2021 International Preliminary Report on Patentability dated May 2, 2023.
PCT/US2021/057135 filed Oct. 28, 2021 International Search Report and Written Opinion dated Mar. 11, 2022.
PCT/US2023/011173 filed Jan. 19, 2023 International Search Report and Written Opinion dated May 22, 2023.
U.S. Appl. No. 17/240,591, filed Apr. 26, 2021 Non-Final Office Action dated Jun. 8, 2023.
U.S. Appl. No. 17/326,017, filed May 20, 2021 Notice of Allowance dated Jul. 3, 2023.
U.S. Appl. No. 17/358,504, filed Jun. 25, 2021 Restriction Requirement dated Jun. 7, 2023.
U.S. Appl. No. 17/360,694, filed Jun. 28, 2021 Restriction Requirement dated Jul. 20, 2023.
U.S. Appl. No. 17/392,061, filed Aug. 2, 2021 Non-Final Office Action dated Jul. 17, 2023.
PCT/US2020/048583 filed Aug. 28, 2020 International Search Report and Written Opinion dated Nov. 13, 2020.
PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.
PCT/US2021/014700 filed Jan. 22, 2021 International Search Report and Written Opinion dated Jun. 29, 2021.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/039084 filed Jun. 25, 2021 International Search Report and Written Opinion dated Jan. 10, 2022.
PCT/US2021/039843 filed Jun. 30, 2021 International Search Report and Written Opinion dated Nov. 11, 2021.
PCT/US2021/044029 filed Jul. 30, 2021 International Search Report and Written Opinion dated Dec. 9, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Final Office Action dated Jan. 25, 2022.
U.S. Appl. No. 16/398,020, filed Apr. 29, 2019 Non-Final Office Action dated May 11, 2021.
U.S. Appl. No. 17/077,728, filed Oct. 22, 2020 Non-Final Office Action dated Feb. 9, 2022.

(56) References Cited

OTHER PUBLICATIONS

U.S. Appl. No. 16/398,020, filed Apr. 29, 2019 Notice of Allowance dated May 20, 2024.
U.S. Appl. No. 17/234,611, filed Apr. 19, 2021 Non-Final Office Action dated Apr. 23, 2024.
U.S. Appl. No. 17/240,591, filed Apr. 26, 2021 Advisory Action dated Feb. 22, 2024.
U.S. Appl. No. 17/240,591, filed Apr. 26, 2021 Non-Final Office Action dated Jun. 4, 2024.
U.S. Appl. No. 17/358,504, filed Jun. 25, 2021 Final Office Action dated Mar. 13, 2024.
U.S. Appl. No. 17/360,694, filed Jun. 28, 2021 Non-Final Office Action dated Feb. 14, 2024.
U.S. Appl. No. 17/390,682, filed Jul. 30, 2021 Final Office Action dated May 6, 2024.
U.S. Appl. No. 17/390,682, filed Jul. 30, 2021 Non-Final Office Action dated Jul. 5, 2024.
U.S. Appl. No. 17/392,061, filed Aug. 2, 2021 Advisory Action dated Feb. 14, 2024.
U.S. Appl. No. 17/392,061, filed Aug. 2, 2021 Non-Final Office Action dated Apr. 23, 2024.
U.S. Appl. No. 17/513,789, filed Oct. 28, 2021 Final Office Action dated Jul. 9, 2024.
U.S. Appl. No. 17/557,924, filed Dec. 21, 2021 Final Office Action dated Feb. 29, 2024.
U.S. Appl. No. 17/240,591, filed Apr. 26, 2021 Final Office Action dated Aug. 14, 2024.
U.S. Appl. No. 17/358,504, filed Jun. 25, 2021 Notice of Allowance dated Jul. 17, 2024.
U.S. Appl. No. 17/557,924, filed Dec. 21, 2021 Non-Final Office Action dated Aug. 20, 2024.

* cited by examiner

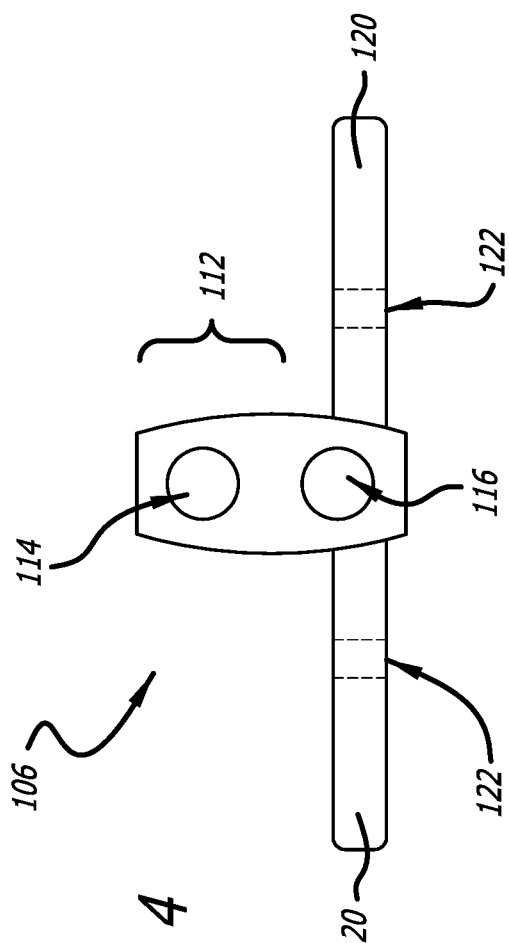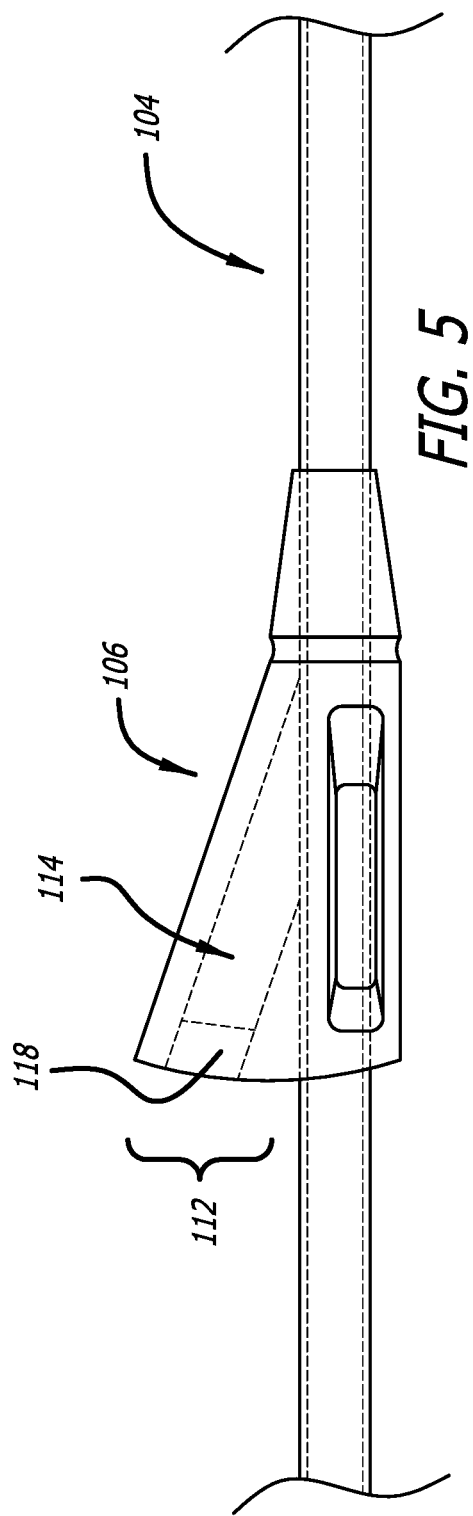

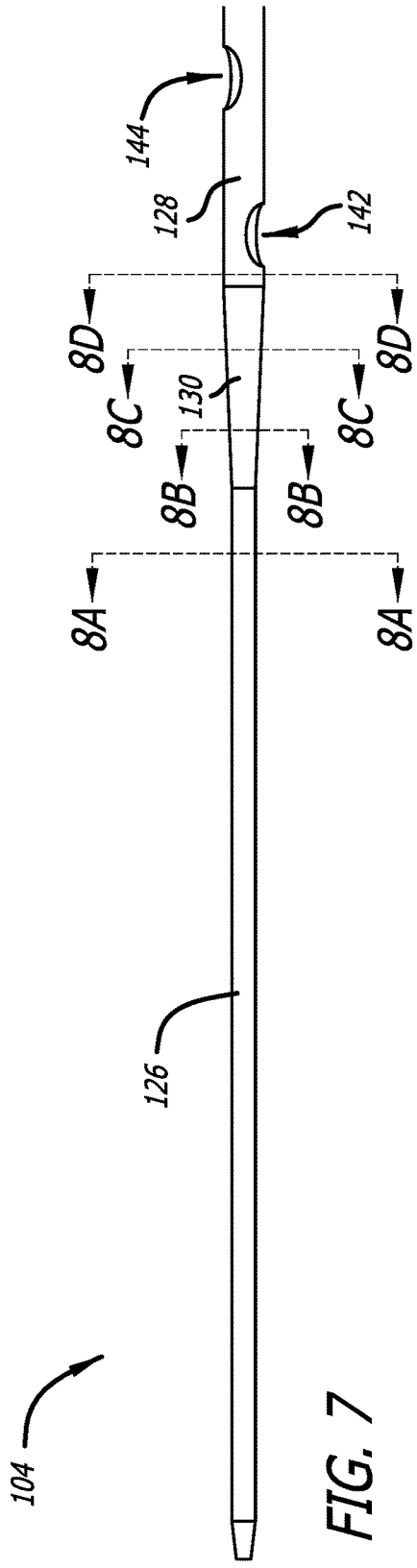
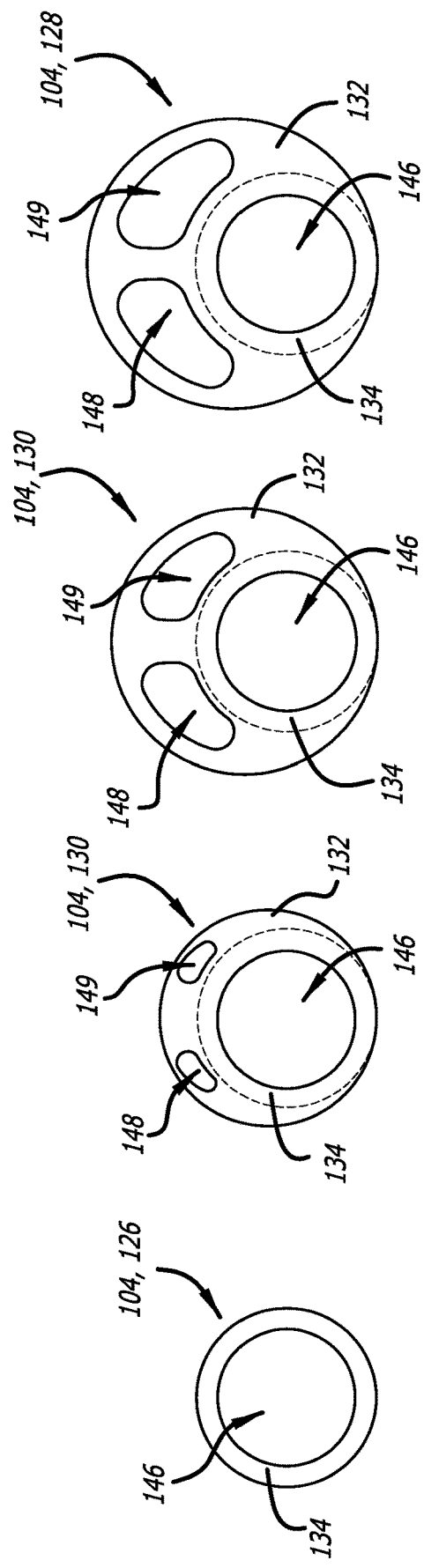

RAPIDLY INSERTABLE CENTRAL CATHETERS, ASSEMBLIES, AND METHODS THEREOF

PRIORITY

This application claims the benefit of priority to U.S. Provisional Application No. 63/126,997, filed Dec. 17, 2020, which is incorporated by reference in its entirety into this application.

BACKGROUND

The Seldinger technique utilizes a number of steps and medical devices (e.g., a needle, a scalpel, a guidewire, an introducer sheath, a dilator, etc.) for introducing central venous catheters ("CVCs") and the like into patients and advancing such catheters through vasculatures of the patients. While the Seldinger technique is effective, the number of steps are time consuming, handling the number of medical devices is awkward, and both of the foregoing can lead to patient trauma. In addition, there is a relatively high potential for touch contamination due to the number of medical devices that need to be interchanged during the number of steps of the Seldinger technique. As such, there is a need to reduce the number of steps and medical devices involved in introducing a catheter into a patient and advancing the catheter through a vasculature thereof.

Disclosed herein are rapidly insertable central catheters ("RICCs"), RICC assemblies, and methods thereof that address the foregoing.

SUMMARY

Disclosed herein is a rapidly insertable central catheter ("RICC") including, in some embodiments, a catheter tube, a suture wing disposed over a medial portion of the catheter tube, a hub coupled to a proximal portion of the catheter tube, and a number of extension legs extending from the hub. The catheter tube includes a first section in a distal portion of the catheter tube and a second section proximal of the first section. The suture wing includes a projection opposite a patient-facing side of the suture wing and a needle through hole through the projection. The needle through hole is configured to accept a needle therethrough for insertion of the needle into a primary lumen of the catheter tube, which passes through a catheter-tube through hole through the suture wing. The number of extension legs are equal to a number of lumens extending through the RICC.

In some embodiments, the suture wing further includes a septum disposed in the needle through hole. The septum is configured to provide a fluid-tight seal for the needle through hole during a percutaneous puncture with the needle disposed in the primary lumen of the catheter tube. The septum is also configured to provide a fluid-tight seal for the needle through hole subsequent to withdrawal of the needle from the needle through hole after the percutaneous puncture.

In some embodiments, the first section of the catheter tube is of a first polymeric material having a first durometer and the second section of the catheter tube is of at least a second polymeric material having a second durometer less than the first durometer.

In some embodiments, each polymeric material of the first and second polymeric materials is a polyurethane.

In some embodiments, the second section includes an outer layer of the catheter tube extruded over an inner layer of the catheter tube such that an outer diameter of the catheter tube is larger in the second section than the first section.

In some embodiments, the catheter tube further includes a bump demarcating a third section of the catheter tube proximal of the second section. The third section has a larger outer diameter than both the first and second sections of the catheter tube.

In some embodiments, the suture wing is disposed over the bump of the catheter tube such that the needle through hole aligns with a needle eyelet in the catheter tube and the catheter tube proximal of the suture wing has a larger outer diameter than the catheter tube distal of the suture wing.

In some embodiments, the RICC is a triluminal catheter including a trifurcated hub as the hub and three extension legs for the number of extension legs extending from the hub. Each extension leg of the three extension legs includes a Luer connector coupled to a proximal portion of the extension leg.

In some embodiments, the RICC includes the primary lumen extending from an opening in a proximal end of a first Luer connector to an opening in a distal end of the first section of the catheter tube, a secondary lumen extending from an opening in a proximal end of a second Luer connector to a first eyelet in a distal portion of the second section of the catheter tube, and a tertiary lumen extending from an opening in a proximal end of a third Luer connector to a second eyelet in the distal portion of the second section of the catheter tube proximal of the first eyelet.

Also disclosed herein is a RICC assembly including, in some embodiments, a RICC and a needle preloaded in the RICC. The RICC includes a catheter tube, a suture wing disposed over a medial portion of the catheter tube, and a hub coupled to a proximal portion of the catheter tube. The catheter tube includes a first section in a distal portion of the catheter tube and a second section proximal of the first section. The suture wing includes a projection opposite a patient-facing side of the suture wing and a needle through hole through the projection. The catheter tube passes through a catheter-tube through hole through the suture wing, and the needle is inserted into a primary lumen of the catheter tube by way of the needle through hole of the suture wing.

In some embodiments, a distal tip of the needle extends past a distal end of the catheter tube for a percutaneous puncture with the needle.

In some embodiments, the RICC assembly further includes a guidewire preloaded in the RICC. The guidewire is inserted into the primary lumen of the catheter tube proximal of an entry point of the needle in the primary lumen of the catheter tube.

In some embodiments, the suture wing further includes a septum disposed in the needle through hole. The septum is configured to provide a fluid-tight seal for the needle through hole during a percutaneous puncture with the needle disposed in the primary lumen of the catheter tube. The septum is also configured to provide a fluid-tight seal for the needle through hole subsequent to withdrawal of the needle from the needle through hole after the percutaneous puncture.

In some embodiments, the first section of the catheter tube is of a first polymeric material having a first durometer and the second section of the catheter tube is of at least a second polymeric material having a second durometer less than the first durometer.

In some embodiments, each polymeric material of the first and second polymeric materials is a polyurethane.

In some embodiments, the second section includes an outer layer of the catheter tube extruded over an inner layer of the catheter tube such that an outer diameter of the catheter tube is larger in the second section than the first section.

In some embodiments, the catheter tube further includes a bump demarcating a third section of the catheter tube less proximal of the second section. The third section has a larger outer diameter than both the first and second sections of the catheter tube.

In some embodiments, the suture wing is disposed over the bump of the catheter tube such that the needle through hole aligns with a needle eyelet in the catheter tube and the catheter tube proximal of the suture wing has a larger outer diameter than the catheter tube distal of the suture wing.

In some embodiments, the RICC is a triluminal catheter including a trifurcated hub as the hub and three extension legs extending from the hub. Each extension leg of the three extension legs includes a Luer connector coupled to a proximal portion of the extension leg.

In some embodiments, the RICC includes the primary lumen extending from an opening in a proximal end of a first Luer connector to an opening in a distal end of the first section of the catheter tube, a secondary lumen extending from an opening in a proximal end of a second Luer connector to a first eyelet in a distal portion of the second section of the catheter tube, and a tertiary lumen extending from an opening in a proximal end of a third Luer connector to a second eyelet in the distal portion of the second section of the catheter tube proximal of the first eyelet.

Also disclosed herein is a method for introducing a RICC into a blood-vessel lumen of a patient. The method includes, in some embodiments, a RICC assembly-obtaining step, a needle tract-establishing step, RICC-advancing step, and a needle-withdrawing step. The RICC assembly-obtaining step includes obtaining a RICC assembly. The RICC assembly includes the RICC and a needle preloaded in the RICC in a ready-to-introduce state of the RICC assembly. The RICC includes a catheter tube, a suture wing disposed over a medial portion of the catheter tube, and a hub coupled to a proximal portion of the catheter tube. A shaft of the needle extends through a needle through hole through the suture wing and a primary lumen of the catheter tube in the ready-to-introduce state of the RICC assembly. In addition, a distal tip of the needle extends beyond a distal end of the catheter tube in the ready-to-introduce state of the RICC assembly. The needle tract-establishing step includes establishing a needle tract from an area of skin to the blood-vessel lumen with the distal tip of the needle. The RICC-advancing step includes advancing a distal portion of the catheter tube into the blood-vessel lumen over the needle. The needle-withdrawing step includes withdrawing the needle from the RICC by way of the needle through hole of the suture wing.

In some embodiments, the method further includes a syringe-connecting step and a blood-aspirating step. The syringe-connecting step is optional in that it includes connecting a syringe to the needle if the syringe is not already connected to the needle in the ready-to-introduce state of the RICC assembly. The blood-aspirating step includes aspirating blood with the syringe before the needle-withdrawing step. The blood-aspirating step confirms the distal tip of the needle is disposed in the blood-vessel lumen.

In some embodiments, the method further includes a guidewire-advancing step. The guidewire-advancing step includes advancing a guidewire into the blood-vessel lumen beyond the distal end of the catheter tube after the needle-withdrawing step. The guidewire is preloaded in the RICC proximal of an entry point of the needle in the primary lumen of the catheter tube in the ready-to-introduce state of the RICC assembly.

In some embodiments, the catheter tube includes a first section of a first polymeric material having a first durometer and a second section proximal of the first section of at least a second polymeric material having a second durometer less than the first durometer. The catheter tube is thusly configured with a column strength for advancing at least the distal portion of the catheter tube into the blood-vessel lumen without buckling.

These and other features of the concepts provided herein will become more apparent to those of skill in the art in view of the accompanying drawings and following description, which describe particular embodiments of such concepts in greater detail.

DRAWINGS

FIG. 4 illustrates an end view of a suture wing of the RICC in accordance with some embodiments.

FIG. 5 illustrates a side view of the suture wing over a catheter tube of the RICC in accordance with some embodiments.

FIG. 7 illustrates a distal portion of the catheter tube of the RICC of FIG. 3 in accordance with some embodiments.

FIG. 8A illustrates a transverse cross section of a first section of the catheter tube in accordance with some embodiments.

FIG. 8B illustrates a transverse cross section of a transition between the first section and a second section of the catheter tube in accordance with some embodiments.

FIG. 8C illustrates another transverse cross section of the transition between the first section and the second section of the catheter tube in accordance with some embodiments.

FIG. 8D illustrates a transverse cross section of the second section of the catheter tube in accordance with some embodiments.

DESCRIPTION

Figure 1:
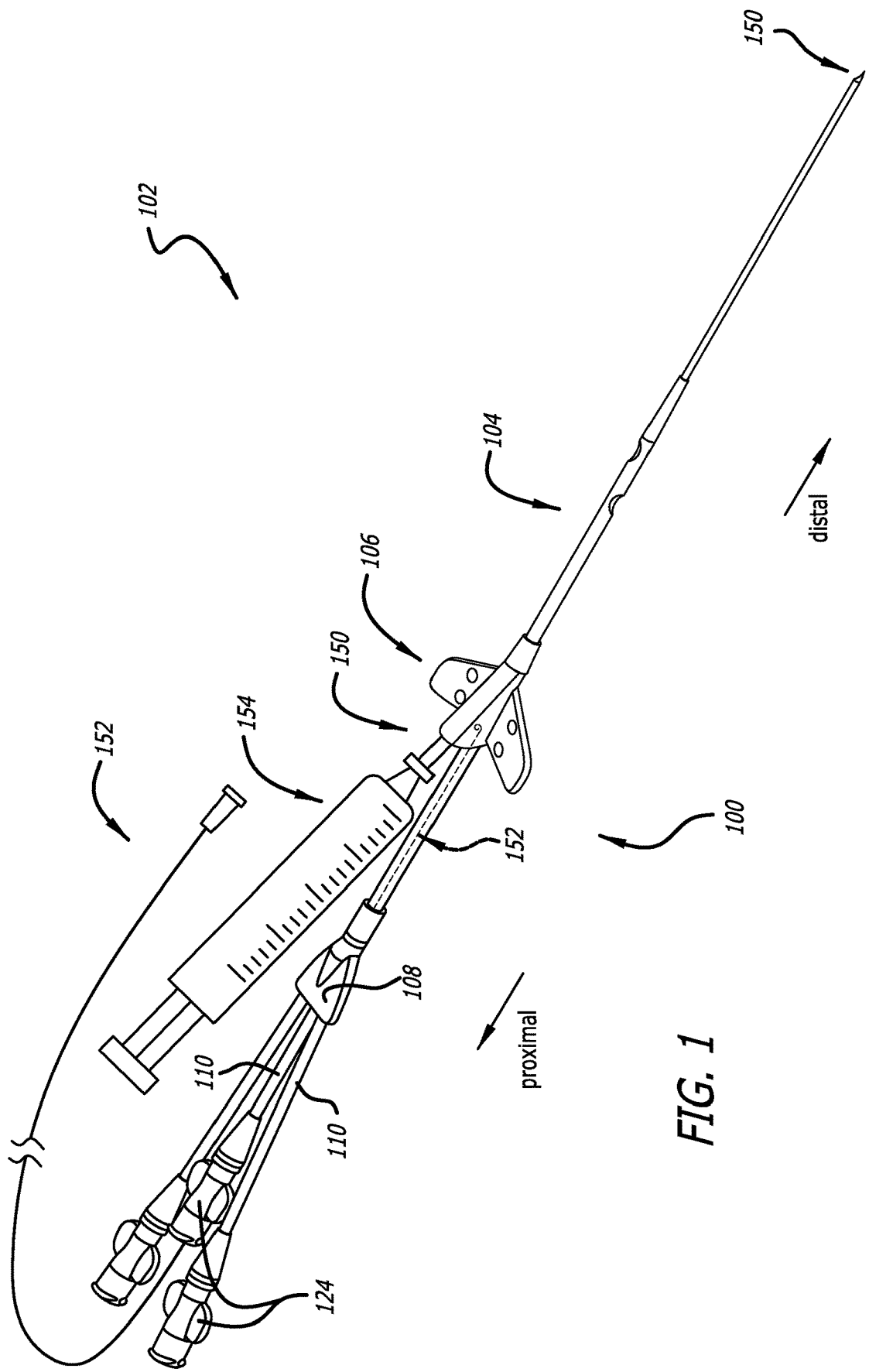
FIG. 1 illustrates a RICC assembly in an assembled, ready-to-introduce state in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need to reduce the number of steps and medical devices involved in introducing a catheter into a patient and advancing the catheter through a vasculature thereof. Disclosed herein are RICCs, RICC assemblies, and methods thereof that address the foregoing.

Rapidly Insertable Central Catheters

Figure 2:
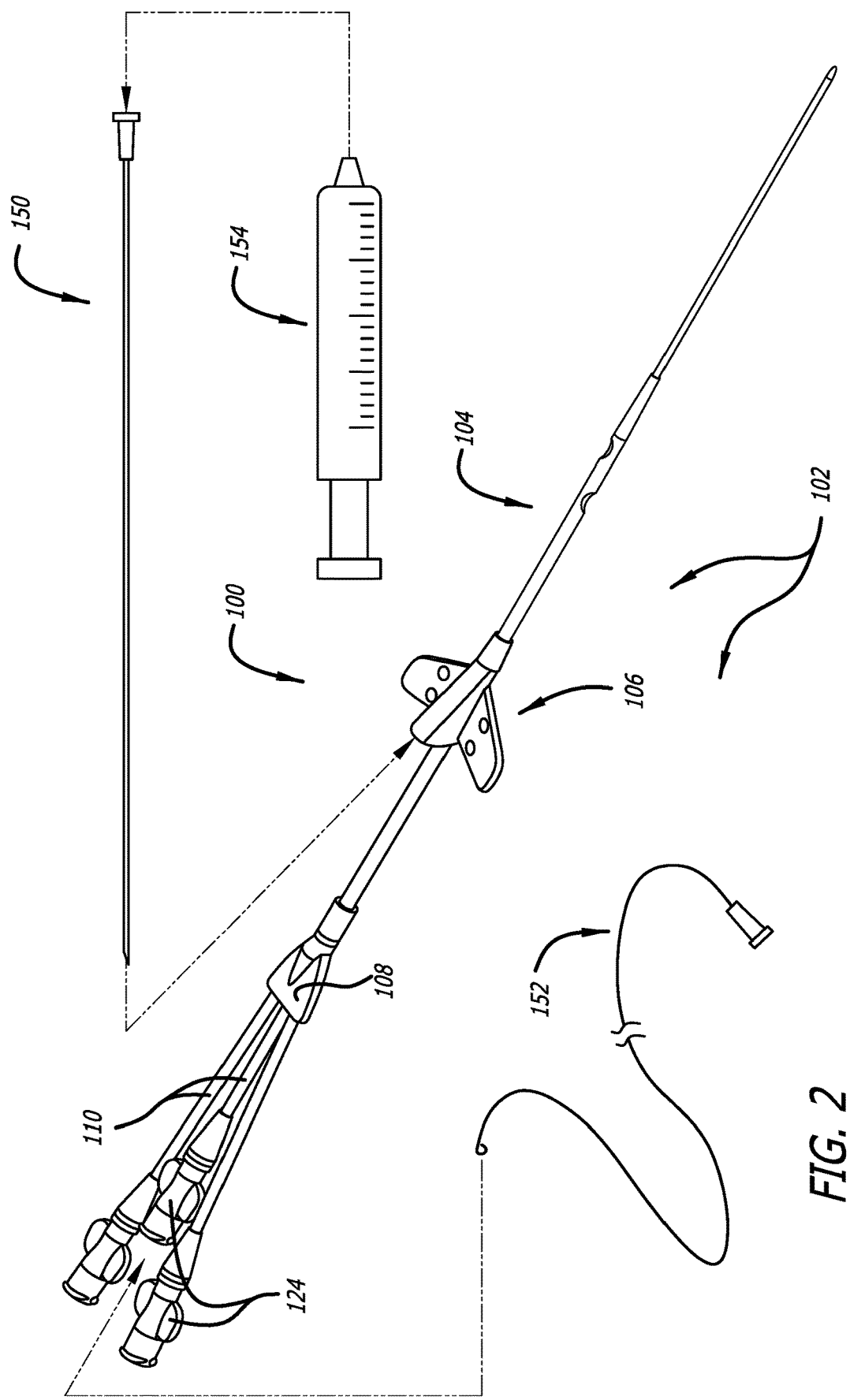
FIG. 2 illustrates the RICC assembly in a disassembled state in accordance with some embodiments.
Figure 3:
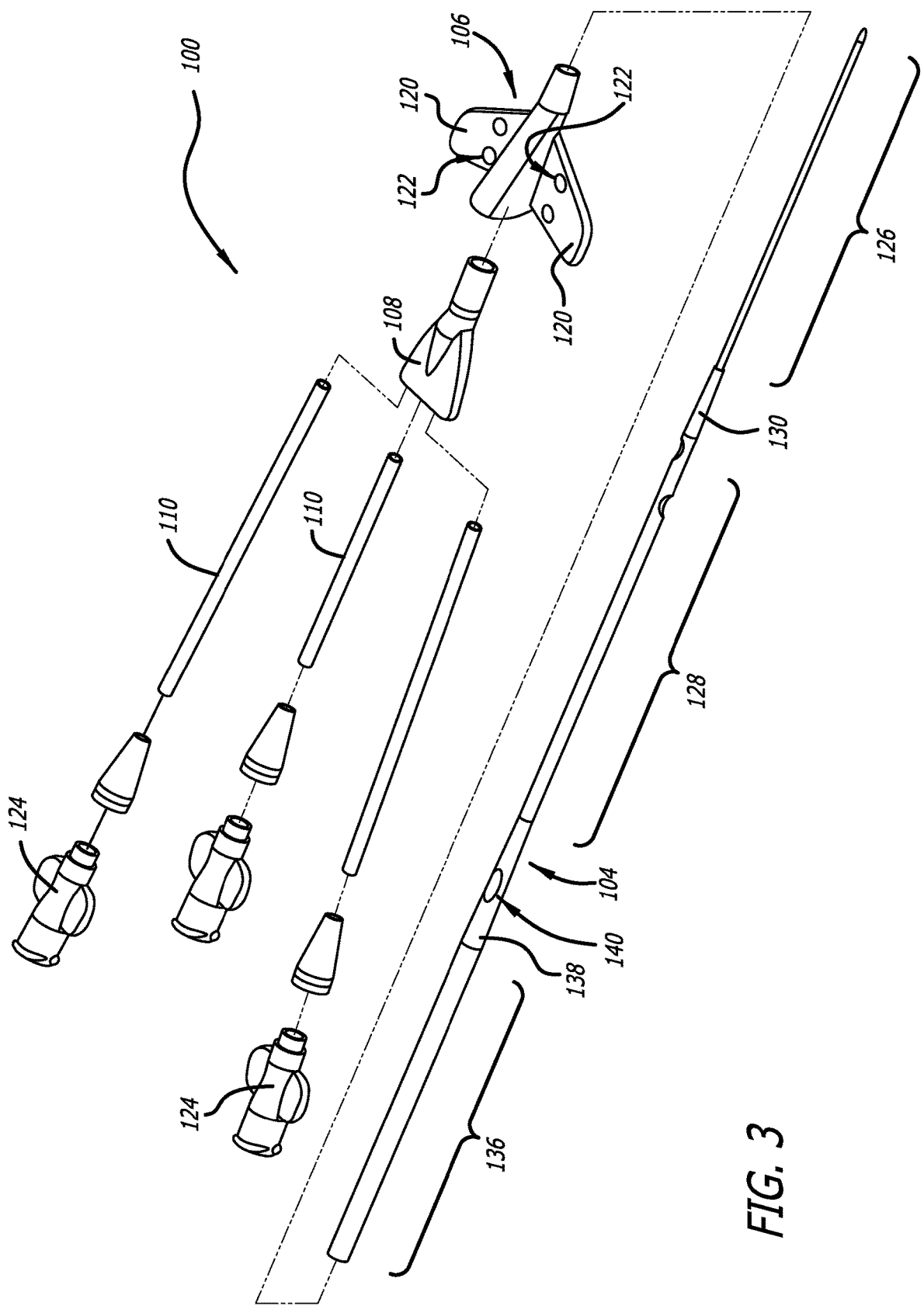
FIG. 3 illustrates a RICC in a disassembled state in accordance with some embodiments.

FIGS. 1 and 2 illustrate a RICC 100 in a RICC assembly 102 in accordance with some embodiments. FIG. 3 illustrates the RICC 100 in a disassembled state in accordance with some embodiments.

As shown, the RICC 100 includes a catheter tube 104, a suture wing 106, a hub 108, and a number of extension legs 110 extending from the hub 108.

The suture wing 106 is disposed over a medial portion of the catheter tube 104 between a proximal portion and a distal portion of the catheter tube 104. The suture wing 106 includes a projection 112 opposite a patient-facing side of the suture wing 106 and a needle through hole 114 through the projection 112. The needle through hole 114 is configured to accept a needle (e.g., the needle 150) therethrough for insertion of the needle into a primary lumen of the RICC 100, specifically the primary catheter-tube lumen 146 of the catheter tube 104, which catheter tube 104 passes through a catheter-tube through hole 116 through the suture wing 106.

The suture wing 106 further includes a septum 118 disposed in the needle through hole 114. The septum 118 is configured to provide a fluid-tight seal for the needle through hole 114 during a percutaneous puncture with the needle (e.g., the needle 150) when disposed in the primary lumen of the RICC 100 (e.g., the primary catheter-tube lumen 146 of the catheter tube 104) such as in the ready-to-introduce state of the RICC assembly 102 set forth below. The septum 118 is also configured to provide a fluid-tight seal for the needle through hole 114 subsequent to withdrawal of the needle from the needle through hole 114 after the percutaneous puncture.

The suture wing 106 includes a pair of wings 120 including a number of wing through holes 122 for suturing the suture wing 106 to a patient. Each wing of the pair of wings 120 can include one wing through hole, two wing through holes, three wing through holes, or four wing through holes for suturing the suture wing 106 to a patient.

Figure 6:
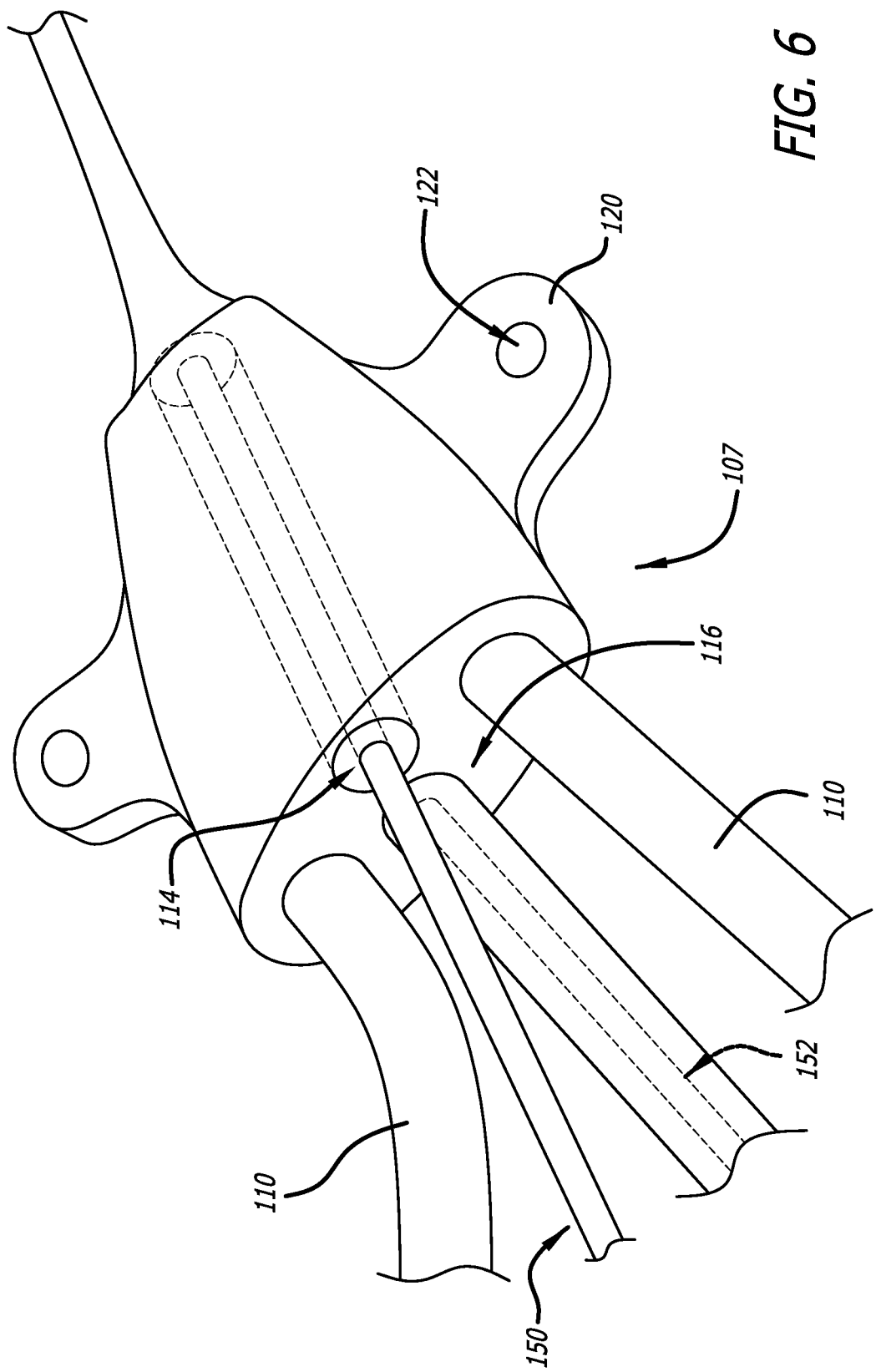
FIG. 6 illustrates an alternative suture wing-and-hub combination of a RICC in accordance with some embodiments.

FIG. 6 illustrates an alternative suture wing-and-hub combination 107 of the RICC 100 in accordance with some embodiments.

As shown, the suture wing-and-hub combination 107, like the suture wing 106, includes the needle through hole 114 configured to accept a needle (e.g., the needle 150) therethrough for insertion of the needle into the primary lumen of the RICC 100, specifically the primary catheter-tube lumen 146 of the catheter tube 104, which catheter tube 104 passes through the catheter-tube through hole 116 through the suture wing 106.

Each of the suture wing 106 and the suture wing-and-hub combination 107 provides an advantage in using the RICC 100 over any other RICC currently in development in that the needle used for establishing a percutaneous puncture with the RICC 100 can be shorter than that needed for the other RICC. Indeed, the other RICC requires a relatively long needle disposed in a primary lumen thereof that extends from an opening in a proximal end of the other RICC (e.g., an opening of a Luer connector) to an opening in a distal end thereof. With such a long needle, it can take a relatively long time to witness a flashback of blood after a percutaneous puncture with the needle. In addition, such a long needle is prone to intraluminal clots. With the RICC 100, however, the needle can be shorter than that needed for the other RICC, thereby providing a relatively short time to witness a flashback of blood after a percutaneous puncture with the needle as well as reduced risk of intraluminal clots in the needle.

The hub 108 is coupled to the proximal portion of the catheter tube 104 such as by insertion of the proximal portion of the catheter tube 104 into a bore in a distal portion of the hub 108. While not shown, the hub 108 also includes a number of bores in a proximal portion of the hub 108 corresponding in number to the number of extension legs 110. The number of bores in the distal portion of the hub 108 are configured to accept insertion of the number of extension legs 110 into the number of bores.

The RICC 100 can be a monoluminal catheter or a multiluminal catheter such as a diluminal catheter, a triluminal catheter, a tetraluminal catheter, a pentaluminal catheter, or a hexaluminal catheter. Accordingly, the hub 108 is either not furcated in accordance with the monoluminal catheter or furcated in accordance with a number of lumens extending through the RICC 100. For example, the hub 108 can be bifurcated for the diluminal catheter or trifurcated for the triluminal catheter. Depending upon a chosen method of manufacturing, the hub 108 can be molded over a number of core pins for a number of fluid pathways longitudinally extending through the hub 108 configured to fluidly connect a number of catheter-tube lumens of the catheter tube 104 to a number of extension-leg lumens of the number of extension legs 110. Alternatively, the hub 108 can be molded over a number of cannulas longitudinally extending through the hub 108 configured to fluidly connect the number of catheter-tube lumens of the catheter tube 104 to the number of extension-leg lumens of the number of extension legs 110.

The number of extension legs 110 extend from the hub 108 by way of their distal portions. The number of extension legs 110 is equal to the number of lumens extending through the RICC 100. For example: If the RICC 100 is a monoluminal catheter, one extension leg extends from the hub 108. If the RICC 100 is a diluminal catheter, two extension legs extend from the hub 108. If the RICC 100 is a triluminal catheter, three extension legs extend from the hub 108.

The RICC 100 further includes a number of Luer connectors 124 for fluidly connecting a number of medical devices to the RICC 100. Each extension leg of the number of extension legs 110 includes a Luer connector of the number of Luer connectors 124 coupled to a proximal portion of the extension leg. Given the foregoing, the number of Luer connectors 124 is equal to the number of extension legs 110, which number of extension legs 110, in turn, is equal to the number of lumens extending through the RICC 100. For example: If the RICC 100 is a monoluminal catheter, one extension leg extends from the hub 108 and one Luer connector is coupled to the one extension leg. If the RICC 100 is a diluminal catheter, two extension legs extend from the hub 108 and two Luer connectors are respectively coupled to the two extension legs. If the RICC 100 is a triluminal catheter, three extension legs extend from the hub 108 and three Luer connectors are respectively coupled to the three extension legs.

The catheter tube 104 includes at least a first section 126 in the distal portion of the catheter tube 104 and a second section 128 proximal of the first section 126 of the catheter tube 104. The catheter tube 104 can include a transition 130 between the first section 126 and the second section 128 of the catheter tube 104 in accordance with the method of manufacturing the catheter tube 104 set forth below. Indeed, in accordance with the manufacturing method set forth below, the transition 130 and the second section 128 of the catheter tube 104 include an outer layer 132 (see FIGS. 8B-8D) of the catheter tube 104 extruded over an inner layer 134 (see FIGS. 8A-8D) of the catheter tube 104 such that an outer diameter of the catheter tube 104 is larger in the second section 128 than the first section 126 of the catheter tube 104 commencing with the transition 130 between the first section 126 and the second section 128 of the catheter tube 104.

The first section 126 of the catheter tube 104 as well as the inner layer 134 of both the transition 130 and the second section 128 of the catheter tube 104 can be formed of a first polymeric material (e.g., polytetrafluoroethylene, polypropylene, or a polyurethane) having a first durometer, while a remainder of the transition 130 and the second section 128 of the catheter tube 104, namely the outer layer 132 thereof, can be formed of a second polymeric material (e.g., polyvinyl chloride, polyethylene, a polyurethane, or silicone) having a second durometer less than the first durometer, more than the first durometer, or substantially equal to the first durometer. For example, each layer of the inner layer 134 and the outer layer 132 of the catheter tube 104 can be made from a different polyurethane (e.g., a same or different diisocyanate or triisocyanate reacted with a different diol or triol, a different diisocyanate or triisocyanate reacted with a same or different diol or triol, etc.) having a different durometer. Polyurethane is advantageous for the catheter tube 104 in that polyurethane can be relatively rigid at room-temperature but become more flexible in vivo at body temperature, which reduces irritation to vessel walls and phlebitis. Polyurethane is also advantageous in that can be less thrombogenic than some other polymers.

Notwithstanding the foregoing, the first section 126 and the second section of the catheter tube 104, which include both the inner layer 134 and the outer layer 132 of the catheter tube 104, can be formed of a same polymeric material (e.g., a polyurethane) with a same durometer provided a column strength of the catheter tube 104 is sufficient to prevent buckling of the catheter tube 104 when inserted into an insertion site and advanced through a vasculature of a patient. The column strength of the catheter tube 104 in any given embodiment is notable in that the column strength makes it possible to rapidly insert the catheter tube 104 into an insertion site and advance the catheter tube 104 through a vasculature of a patient without the using the Seldinger technique.

It should be understood the first durometer and the second durometer can be on different scales (e.g., Type A or Type D). Thus, even if the second durometer of the second polymeric material is less than the first durometer of the first polymeric material, the second durometer might not be numerically less than the first durometer. Likewise, even if the second durometer of the second polymeric material is more than the first durometer of the first polymeric material, the second durometer might not be numerically more than the first durometer. That said, the hardness of the second polymeric material can still be respectively less or more than the hardness of the first polymeric material as the different scales—each of which ranges from 0 to 100—are designed for characterizing different materials in groups of the materials having a like hardness.

The catheter tube 104 can include a third section 136 proximal of the second section 128 of catheter tube 104 including a bumped diameter demarcated by a bump 138 in the medial portion of the catheter tube 104. The third section 136 of the catheter tube 104 has a larger outer diameter than both the first section 126 and the second section 128 of the catheter tube 104. The suture wing 106 can be disposed over the bump 138 as shown among FIGS. 1 and 2 such that the needle through hole 114 aligns with an optional needle eyelet 140 in the catheter tube 104. Thus, the catheter tube 104 proximal of the suture wing 106 (also known as a catheter-tube extension herein) has a larger outer diameter than the catheter tube 104 distal of the suture wing 106. The larger outer diameter of the third section 136 of the catheter tube 104 proximal of the suture wing 106 provides a thicker, more kink-resistant catheter-tube wall useful for bending the hub 108 and the number of extension legs 110 away from a head or neck of a patient while the RICC 100 is in use. In addition, any lumens present in the catheter tube 104 can have a greater diameter in the third section 136 of catheter tube 104 proximal of the suture wing 106 than distal of the suture wing 106. This prevents flow rate reduction, particularly when the third section 136 of the catheter tube 104 proximal of the suture wing 106 is bent away from a head or neck of a patient.

The catheter tube 104 between the suture wing 106 and the hub 108 can have a reverse taper in which the larger outer diameter of the catheter tube 104 continues to increase from the suture wing 106 to the hub 108. In other words, the catheter tube 104 tapers from the hub 108 to the suture wing 106 but continues to have a larger outer diameter than the catheter tube 104 distal of the suture wing 106. In association with the continuously increasing outer diameter of the catheter tube 104 from the suture wing 106 to the hub 108, the catheter-tube wall can continuously increase in thickness, any lumens of the catheter tube 104 can continuously increase in cross-sectional area, or a combination thereof. Consequently, the catheter tube 104 between the suture wing 106 and the hub 108 can be more resistant to kinks and flow rate reduction, particularly when the catheter tube 104 proximal of the suture wing 106 is bent away from a head or neck of a patient. Notwithstanding the foregoing, the catheter tube 104 between the suture wing 106 and the hub 108 can alternatively have a constant diameter from the suture wing 106 to the hub 108.

Advantageously, the catheter tube 104 between the suture wing 106 and the hub 108, namely the third section 136 of the catheter tube 104 or the catheter-tube extension, is a single catheter tube configured to abate bacterial ingress between a dressing applied over the suture wing 106 and skin of a patient. Existing CVCs or peripherally inserted central catheters ("PICCs") have multiple extension legs extending from suture wing-hub combinations common to the CVCs and PICCs. The multiple extension legs in the CVCs or PICCs provide multiple pathways under the dressing for microbial ingress. The catheter tube 104 being a single catheter tube between at least the suture wing 106 and the hub 108 enables the dressing to be pinched more tightly around the catheter tube 104 than possible for the multiple extension legs of the existing CVCs or PICCs. For example, the dressing can be easily wrapped around an entirety of the catheter tube 104 and pinched together under the catheter tube 104 between the catheter tube 104 and the patient. In contrast, even wrapping the dressing around the multiple extension legs of the existing CVCs or PICCs as described for the catheter-tube extension leaves gaps between adjacent extension tubes for bacterial ingress. Thus, the catheter tube 104 being a single catheter tube limits bacterial ingress between the dressing applied over the suture wing 106 and the skin of the patient.

The catheter tube 104 between the suture wing 106 and the hub 108, again the third section 136 of the catheter tube 104 or the catheter-tube extension, is also configured to mitigate patient discomfort from proximity of the number or extension legs 110 to a head or neck of the patient. As set forth above, the third section 136 of the catheter tube 104 proximal of the suture wing 106 provides a thicker, more kink-resistant catheter-tube wall; however, the third section 136 of the catheter tube 104 is flexible enough to enable the catheter tube 104 to be bent away from the head or neck of the patient and secured to the patient for his or her comfort.

FIG. 7 illustrates a distal portion of the catheter tube 104 of the RICC 100 in accordance with some embodiments. FIGS. 8A-8D illustrate various transverse cross sections of the catheter tube 104 in accordance with some embodiments.

Again, the RICC 100 can be a monoluminal catheter or a multiluminal catheter such as a diluminal catheter, a triluminal catheter, a tetraluminal catheter, a pentaluminal catheter, or a hexaluminal catheter. The catheter tube 104 can correspondingly be a monoluminal catheter tube or a multiluminal catheter tube such as a diluminal catheter tube, a triluminal catheter tube, a tetraluminal catheter tube, a pentaluminal catheter tube, or a hexaluminal catheter tube.

When the RICC 100 is configured as a triluminal catheter as shown among FIGS. 1-3, 7, and 8A-8D, the RICC 100 includes a primary lumen, a secondary lumen, and a tertiary lumen. The primary lumen extends from an opening in a proximal end of a first Luer connector of the number of Luer connectors 124 to an opening in a tip or distal end of the first section 126 of the catheter tube 104. The secondary lumen extends from an opening in a proximal end of a second Luer connector of the number of Luer connectors 124 to an eyelet 142 in a distal portion of the second section 128 of the catheter tube 104. The tertiary lumen extends from an opening in a proximal end of a third Luer connector of the number of Luer connectors 124 to an eyelet 144 proximal of the eyelet 142 in the distal portion of the second section 128 of the catheter tube 104. Each lumen of the primary lumen, the secondary lumen, and the tertiary lumen is further described in a separate paragraph set forth below.

The primary lumen of the RICC 100 includes fluidly connected luminal sections including a primary catheter-tube lumen 146 extending along an entire length of the catheter tube 104, a primary fluid passageway or primary cannula lumen of the hub 108, a primary extension-leg lumen of a first extension leg of the number of extension legs 110, and a primary Luer-connector lumen of the first Luer connector of the number of Luer connectors 124.

The secondary lumen of the RICC 100 includes fluidly connected luminal sections including a secondary catheter-tube lumen 148, which proximally extends from the eyelet 142 in the distal portion of the second section 128 of the catheter tube 104 along a remainder of the catheter tube 104. The fluidly connected luminal sections of the secondary lumen of the RICC 100 further include a secondary fluid passageway or secondary cannula lumen of the hub 108, a secondary extension-leg lumen of a second extension leg of the number of extension legs 110, and a secondary Luer-connector lumen of the second Luer connector of the number of Luer connectors 124.

The tertiary lumen of the RICC 100 includes fluidly connected luminal sections including a tertiary catheter-tube lumen 149, which proximally extends from the eyelet 144 in the distal portion of the second section 128 of the catheter tube 104 along a remainder of the catheter tube 104. The fluidly connected luminal sections of the tertiary lumen of the RICC 100 further include a tertiary fluid passageway or tertiary cannula lumen of the hub 108, a tertiary extension-leg lumen of a third extension leg of the number of extension legs 110, and a tertiary Luer-connector lumen of the third Luer connector of the number of Luer connectors 124.

When the RICC 100 is configured as a diluminal catheter, the RICC 100 includes a primary lumen and a secondary lumen. Like the RICC 100 when configured as the triluminal catheter, the primary lumen extends from the opening in the proximal end of the first Luer connector of the number of Luer connectors 124 to the opening in the tip or the distal end of the first section 126 of the catheter tube 104. The secondary lumen extends from the opening in the proximal end of the second Luer connector of the number of Luer connectors 124 to the eyelet 142 in the distal portion of the second section 128 of the catheter tube 104. Because the primary lumen and the secondary lumen of the RICC 100 configured as the diluminal catheter are analogous to the primary lumen and the secondary lumen of the RICC 100 configured as the triluminal catheter, additional detail for each lumen of the primary lumen and the secondary lumen of the RICC 100 configured as the diluminal catheter can be discerned from the description set forth above for the primary lumen and the secondary lumen of the RICC 100 configured as the triluminal catheter.

When the RICC 100 is configured as a monoluminal catheter, the RICC 100 includes a single lumen, which single lumen is also known as a primary lumen herein for consistency with description set forth above. Like the RICC 100 when configured as the triluminal catheter, the primary lumen extends from the opening in the proximal end of the first Luer connector of the number of Luer connectors 124 to the opening in the tip or the distal end of the first section 126 of the catheter tube 104. Because the primary lumen of the RICC 100 configured as the monoluminal catheter is analogous to the primary lumen of the RICC 100 configured as the triluminal catheter, additional detail for the primary lumen of the RICC 100 configured as the monoluminal catheter can be discerned from the description set forth above for the primary lumen of the RICC 100 configured as the triluminal catheter.

RICC Assemblies

FIGS. 1 and 2 illustrate the RICC assembly 102 in accordance with some embodiments. In particular, FIG. 1 illustrates the RICC assembly 102 in an assembled, ready-to-introduce state in accordance with some embodiments, whereas FIG. 2 illustrates the RICC assembly 102 in a disassembled state in accordance with some embodiments.

As shown, the RICC assembly 102 includes at least the RICC 100 and a needle 150 preloaded in the RICC 100 in the ready-to-introduce state of the RICC assembly 102. Optionally, the RICC assembly 102 includes a guidewire 152 preloaded in the RICC 100, a syringe 154 coupled to a hub of the needle 150, or both the guidewire 152 and the syringe 154 in the ready-to-introduce state of the RICC assembly 102. In a packaged state of the RICC assembly 102, the RICC assembly 102 resembles the ready-to-introduce state of the RICC assembly 102; however, if the syringe 154 is present in a package including the RICC assembly 102, the syringe 154 need not be coupled to the hub of the needle 150. Indeed, the syringe 154 can be packaged alongside a remainder of the RICC assembly 102 in the packaged state of the RICC assembly 102.

The needle 150 is inserted into the primary lumen of the RICC 100 by way of the needle through hole 114 of the suture wing 106 in the ready-to-introduce state of the RICC assembly 102. Specifically, the needle 150 is inserted into the primary catheter-tube lumen 146 of the catheter tube 104, which catheter tube 104 passes through the catheter-tube through hole 116 through the suture wing 106. In addition, a distal tip of the needle 150 including a bevel extends past the distal end of the catheter tube 104 for a percutaneous puncture with the needle 150.

The guidewire 152 is inserted into the primary lumen of the RICC 100 by way of the opening in the proximal end of the first Luer connector of the number of Luer connectors 124 in the ready-to-introduce state of the RICC assembly 102. A distal end of the guidewire 152 is proximal of an entry point of the needle 150 in the primary lumen of the RICC 100, specifically the primary catheter-tube lumen 146 of the catheter tube 104. Such placement of the guidewire 152 in the ready-to-introduce state of the RICC assembly 102 enables the guidewire 152 to be immediately advanced into a blood-vessel lumen of a patient after a percutaneous puncture with the needle 150 and withdrawal thereof from the RICC 100. The foregoing placement of the guidewire 152 in the ready-to-introduce state of the RICC assembly 102 is advantageous over placement of the guidewire 152 in the needle 150 because it allows the guidewire 152 to have a larger diameter than that allowed by the needle 150, which larger diameter provides more stability for the catheter tube 104 when maneuvered over the guidewire 152.

Methods

Methods of the RICCs and RICC assemblies set forth above include methods of making and using the RICCs and RICC assemblies. An example method for making the RICC 100 is set forth below followed by a method for using the RICC assembly 102, specifically a method for introducing the RICC 100 into a blood-vessel lumen of a patient.

A method for making the RICC 100 includes one or more catheter tube-manufacturing steps for manufacturing the catheter tube 104, one or more extruding steps of extruding one or more extrudable components other than the catheter tube 104 such as the number of extension legs 110, one or more molding steps of molding one or more moldable components, and one or more assembling steps of assembling the RICC 100 or any portion thereof by coupling the extrudable components including the catheter tube 104 and the moldable components together.

Figure 9:
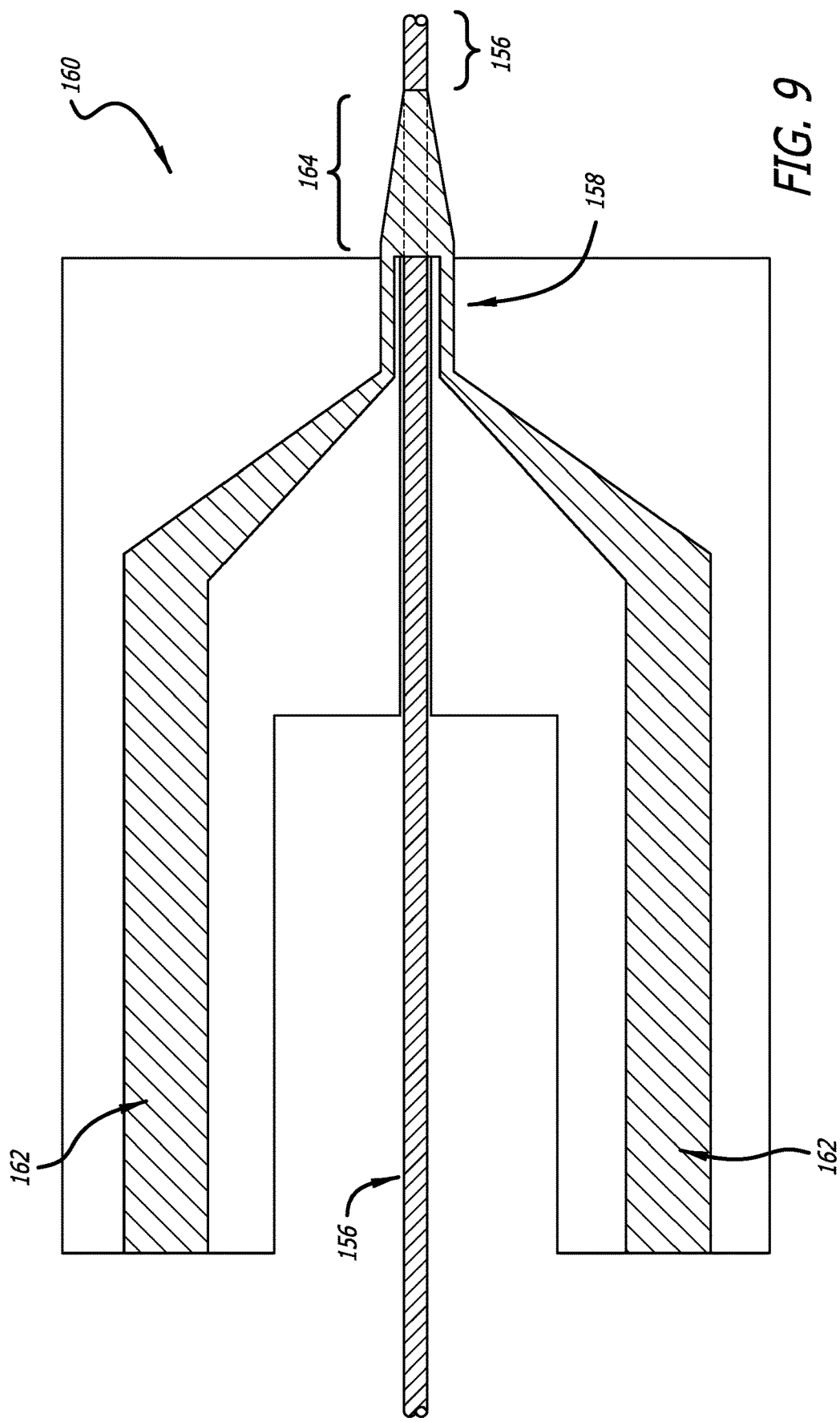
FIG. 9 illustrates a portion of the manufacturing of the catheter tube in accordance with some embodiments.

FIG. 9 illustrates a portion of the manufacturing of the catheter tube 104 in accordance with some embodiments.

The one-or-more catheter tube-manufacturing steps include an inner-layer forming step. The inner-layer forming step includes forming the inner layer 134 of the catheter tube 104 by extruding monoluminal tubing 156 of the first polymeric material.

The one-or-more catheter tube-manufacturing steps further include an inserting step. The inserting step includes inserting an end of the monoluminal tubing 156 through a die 158 of an extruder 160.

The one-or-more catheter tube-manufacturing steps further include a second-layer forming step. The second-layer forming step includes forming the outer layer 132 of the catheter tube 104 by periodically forcing a melt 162 of the second polymeric material through the die 158 around the monoluminal tubing 156, thereby forming output tubing with sections of mixed-layer tubing 164 regularly interspersed with sections of the monoluminal tubing 156.

The one-or-more catheter tube-manufacturing steps can further include a bonding layer-applying step. The bonding layer-applying step includes applying a bonding layer over the monoluminal tubing 156 before forcing the melt 162 of the second polymeric material through the die 158 around the monoluminal tubing 156 in the second-layer forming step.

The one-or-more catheter tube-manufacturing steps further includes a lumen forming step. The lumen forming step includes forming one or more additional lumens (e.g., the secondary catheter-tube lumen 148, the tertiary catheter-tube lumen 149, etc.) to that of the monoluminal tubing 156 by injecting air into the melt 162 of the second polymeric material while forcing the melt 162 of the second polymeric material through the die 158 around the monoluminal tubing 156.

The one-or-more catheter tube-manufacturing steps further includes an eyelet-creating step. The eyelet-creating step includes creating one or more eyelets (e.g., the needle eyelet 140, the eyelet 142, the eyelet 144, etc.) in the sections of the mixed-layer tubing 164 to correspondingly establish one or openings to the primary catheter-tube lumen 146 or the one-or-more additional lumens.

The one-or-more catheter tube-manufacturing steps can further include a bump-forming step. The bump-forming step includes forming bumps (e.g., the bump 138 in the medial portion of the catheter tube 104) in the sections of the mixed-layer tubing 164 by periodically slowing a rate of pulling the output tubing with a puller to increase an outer diameter of the output tubing after the bumps.

The one-or-more catheter tube-manufacturing steps can further include a reverse-tapering step. The reverse-tapering step includes reverse tapering the outer diameter in the sections of the mixed-layer tubing 164 after the bumps by continuously slowing the rate of pulling the output tubing with the puller.

The one-or-more catheter tube-manufacturing steps can further include a cooling step. The cooling step includes pulling the output tubing through a cooling bath with the puller to cool the output tubing.

The one-or-more catheter tube-manufacturing steps further includes a cutting step. The cutting step includes cutting the output tubing in at least the sections of the monoluminal tubing 156 with a cutter to form the catheter tubes such as the catheter tube 104.

The one-or-more extruding steps can include extruding any one or more extension legs of the number of extension legs 110 in accordance with description set forth above for the one-or-more extension legs.

The one-or-more molding steps can include molding any one or more moldable components selected from the suture wing 106 and the hub 108 in accordance with description set forth above for such moldable components. The one-or-more molding steps can further include molding any one or more Luer connectors of the number of Luer connectors 124 in accordance with description set forth above for the one-or-more Luer connectors.

The one-or-more assembling steps of assembling the RICC 100 or any portion thereof can include assembling the RICC 100 in accordance with that shown in FIG. 3 with the understanding a distal portion of the catheter tube 104 is inserted into a proximal portion the suture wing 106.

A method for introducing the RICC 100 into a blood-vessel lumen of a patient includes a RICC assembly-obtaining step, a needle tract-establishing step, first and second RICC-advancing steps, and a needle-withdrawing step.

The RICC assembly-obtaining step includes obtaining the RICC assembly 102. As set forth above, the RICC assembly 102 includes at least the RICC 100 and the needle 150 preloaded in the RICC in the ready-to-introduce state of the RICC assembly 102. Indeed, the shaft of the needle 150 extends through the needle through hole 114 of the suture wing 106 and the primary lumen of the RICC 100, specifically the primary catheter-tube lumen 146 of the catheter tube 104, in the ready-to-introduce state of the RICC assembly 102. In addition, the distal tip of the needle 150 extends beyond the distal end of the catheter tube 104 in the ready-to-introduce state of the RICC assembly 102.

The needle tract-establishing step includes establishing a needle tract from an area of skin to the blood-vessel lumen with the distal tip of the needle 150.

The first RICC-advancing step includes advancing a distal portion of the catheter tube 104 into the blood-vessel lumen over the needle 150.

The needle-withdrawing step includes withdrawing the needle 150 from the RICC 100 by way of the needle through hole 114 of the suture wing 106.

The second RICC-advancing step includes advancing the catheter tube 104 through the vasculature of the patient without having to use the Seldinger technique. For example, if an insertion site is at the right subclavian vein or the right internal jugular vein, the second RICC-advancing step can include inserting the catheter tube 104 farther into the insertion site such that the catheter tube 104 or at least the distal portion thereof is advanced through the right subclavian vein or the right internal jugular vein, a right brachiocephalic vein, and into a superior vena cava. Other insertions sites such as at the left subclavian vein or the left internal jugular vein require advancing the distal portion of the catheter tube 104 through corresponding vasculature. The Seldinger technique need not be used due to the catheter tube 104 having a column strength sufficient to prevent buckling of the catheter tube 104 when inserted into the insertion site and advanced through the vasculature of the patient.

The method can further include a syringe-connecting step and a blood-aspirating step. The syringe-connecting step is optional in that it includes connecting the syringe 154 to the hub of the needle 150 if the syringe 154 is not already connected to the needle 150 in the ready-to-introduce state of the RICC assembly 102. The blood-aspirating step includes aspirating blood with the syringe 154 before the needle-withdrawing step. The blood-aspirating step confirms the distal tip of the needle 150 is disposed in the blood-vessel lumen of the patient.

The method can further include a guidewire-advancing step after the needle-withdrawing step. The guidewire-advancing step includes advancing the guidewire 152 into the blood-vessel lumen of the patient beyond the distal end of the catheter tube 104 after the needle-withdrawing step. As set forth above, the guidewire 152 is preloaded in the RICC 100 proximal of an entry point of the needle 150 in the primary lumen of the RICC 100, specifically the primary catheter-tube lumen 146 of the catheter tube 104, in the ready-to-introduce state of the RICC assembly 102.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A rapidly insertable central catheter ("RICC"), comprising:
    a catheter tube, including:
        a first section in a distal portion of the catheter tube; and
        a second section proximal of the first section;
    a suture wing disposed over a medial portion of the catheter tube and a needle eyelet thereof, the suture wing including:
        a projection opposite a patient-facing side of the suture wing; and
        a needle through hole through the projection configured to accept a needle therethrough for insertion of the needle through the needle eyelet of the catheter tube and into a primary lumen of the catheter tube, the catheter tube passing through a catheter-tube through hole through the suture wing;
    a hub coupled to a proximal portion of the catheter tube; and
    a number of extension legs extending from the hub equal to a number of lumens extending through the RICC.

2. The RICC of claim 1, wherein the suture wing further includes a septum disposed in the needle through hole configured to provide a fluid-tight seal for the needle through hole during a percutaneous puncture with the needle disposed in the primary lumen of the catheter tube or subsequent to withdrawal of the needle from the needle through hole after the percutaneous puncture.

3. The RICC of claim 1, wherein the first section of the catheter tube is of a first polymeric material having a first durometer and at least a portion of the second section of the catheter tube is of a second polymeric material having a second durometer less than the first durometer.

4. The RICC of claim 3, wherein each polymeric material of the first polymeric material and the second polymeric material is a polyurethane.

5. The RICC of claim 1, wherein the second section includes an outer layer of the catheter tube extruded over an inner layer of the catheter tube such that an outer diameter of the catheter tube is larger in the second section than the first section.

6. The RICC of claim 1, wherein the catheter tube further includes a bump demarcating a third section of the catheter tube proximal of the second section, the third section having a larger outer diameter than both the first section and the second section of the catheter tube.

7. The RICC of claim 6, wherein the suture wing is disposed over the bump of the catheter tube such that the needle through hole aligns with the needle eyelet in the catheter tube and the catheter tube proximal of the suture wing has a larger outer diameter than the catheter tube distal of the suture wing.

8. The RICC of claim 1, wherein the RICC is a triluminal catheter including a trifurcated hub as the hub and three extension legs for the number of extension legs extending from the hub, each extension leg of the three extension legs including a Luer connector coupled to a proximal portion of the number of extension legs.

9. The RICC of claim 8, wherein the RICC includes the primary lumen extending from an opening in a proximal end of a first Luer connector to an opening in a distal end of the first section of the catheter tube, a secondary lumen extending from an opening in a proximal end of a second Luer connector to a first eyelet in a distal portion of the second section of the catheter tube, and a tertiary lumen extending from an opening in a proximal end of a third Luer connector to a second eyelet in the distal portion of the second section of the catheter tube proximal of the first eyelet.

10. A rapidly insertable central-catheter ("RICC") assembly, comprising:
a RICC, including:
a catheter tube, including:
a first section in a distal portion of the catheter tube; and
a second section proximal of the first section;
a suture wing disposed over a medial portion of the catheter tube and a needle eyelet thereof, the suture wing including:
a projection opposite a patient-facing side of the suture wing; and
a needle through hole through the projection, the catheter tube passing through a catheter-tube through hole through the suture wing; and
a hub coupled to a proximal portion of the catheter tube; and
a needle preloaded in the RICC, the needle inserted into a primary lumen of the catheter tube by way of the needle eyelet of the catheter tube and the needle through hole of the suture wing.

11. The RICC assembly of claim 10, wherein a distal tip of the needle extends past a distal end of the catheter tube for a percutaneous puncture with the needle.

12. The RICC assembly of claim 10, further comprising a guidewire preloaded in the RICC, the guidewire inserted into the primary lumen of the catheter tube proximal of an entry point of the needle in the primary lumen of the catheter tube.

13. The RICC assembly of claim 10, wherein the suture wing further including a septum disposed in the needle through hole configured to provide a fluid-tight seal for the needle through hole during a percutaneous puncture with the needle disposed in the primary lumen of the catheter tube or subsequent to withdrawal of the needle from the needle through hole after the percutaneous puncture.

14. The RICC assembly of claim 10, wherein the first section of the catheter tube is of a first polymeric material having a first durometer and at least a portion of the second section of the catheter tube is of a second polymeric material having a second durometer less than the first durometer.

15. The RICC assembly of claim 14, wherein each polymeric material of the first polymeric material and the second polymeric material is a polyurethane.

16. The RICC assembly of claim 10, wherein the second section includes an outer layer of the catheter tube extruded over an inner layer of the catheter tube such that an outer diameter of the catheter tube is larger in the second section than the first section.

17. The RICC assembly of claim 10, wherein the catheter tube further includes a bump demarcating a third section of the catheter tube proximal of the second section, the third section having a larger outer diameter than both the first section and the second section of the catheter tube.

18. The RICC assembly of claim 17, wherein the suture wing is disposed over the bump of the catheter tube such that the needle through hole aligns with the needle eyelet in the catheter tube and the catheter tube proximal of the suture wing has a larger outer diameter than the catheter tube distal of the suture wing.

19. The RICC assembly of claim 10, wherein the RICC is a triluminal catheter including a trifurcated hub as the hub and three extension legs extending from the hub, each extension leg of the three extension legs including a Luer connector coupled to a proximal portion of each extension leg.

20. The RICC assembly of claim 19, wherein the RICC includes the primary lumen extending from an opening in a proximal end of a first Luer connector to an opening in a distal end of the first section of the catheter tube, a secondary lumen extending from an opening in a proximal end of a second Luer connector to a first eyelet in a distal portion of the second section of the catheter tube, and a tertiary lumen extending from an opening in a proximal end of a third Luer connector to a second eyelet in the distal portion of the second section of the catheter tube proximal of the first eyelet.

21. A method for introducing a rapidly insertable central-catheter ("RICC") into a blood-vessel lumen of a patient, comprising:
obtaining a RICC assembly, including:
the RICC including a catheter tube, a suture wing disposed over a medial portion of the catheter tube and a needle eyelet thereof, and a hub coupled to a proximal portion of the catheter tube; and
a needle preloaded in the RICC in a ready-to-introduce state of the RICC assembly, a shaft of the needle extending through a needle through hole through the suture wing, the needle eyelet of the catheter tube, and a primary lumen of the catheter tube as well as a distal tip of the needle extending beyond a distal end of the catheter tube;

establishing a needle tract from an area of skin to the blood-vessel lumen with the distal tip of the needle;

advancing a distal portion of the catheter tube into the blood-vessel lumen over the needle; and withdrawing the needle from the RICC by way of the needle through hole of the suture wing.

22. The method of claim 21, further comprising:

connecting a syringe to the needle if the syringe is not already connected to the needle in the ready-to-introduce state of the RICC assembly; and aspirating blood with the syringe before withdrawing the needle from the RICC, thereby confirming the distal tip of the needle is disposed in the blood-vessel lumen.

23. The method of claim 21, further comprising advancing a guidewire into the blood-vessel lumen beyond the distal end of the catheter tube after withdrawing the needle from the RICC, the guidewire preloaded in the RICC proximal of an entry point of the needle in the primary lumen of the catheter tube in the ready-to-introduce state of the RICC assembly.

24. The method of claim 21, wherein the catheter tube includes a first section of a first polymeric material having a first durometer and a second section proximal of the first section of at least a second polymeric material having a second durometer less than the first durometer, the catheter tube thereby configured with a column strength for advancing at least the distal portion of the catheter tube into the blood-vessel lumen without buckling.

* * * * *